United States Patent [19]

Nargund et al.

[11] Patent Number: 5,777,112
[45] Date of Patent: Jul. 7, 1998

[54] PIPERAZINE COMPOUNDS PROMOTE RELEASE OF GROWTH HORMONE

[75] Inventors: Ravi Nargund, East Brunswick, N.J.; Khaled Barakat, Brooklyn, N.Y.; Meng Hsin Chen; Arthur Patchett, both of Westfield, N.J.

[73] Assignee: Merck & Co., Inc. Rahway, N.J.

[21] Appl. No.: 750,759

[22] PCT Filed: Jun. 9, 1995

[86] PCT No.: PCT/US95/07001

§ 371 Date: Dec. 12, 1996

§ 102(e) Date: Dec. 12, 1996

[87] PCT Pub. No.: WO95/34311

PCT Pub. Date: Dec. 21, 1995

Related U.S. Application Data

[63] Continuation of Ser. No. 258,644, Jun. 13, 1994, abandoned.
[51] Int. Cl.$^6$ .................. C07D 413/00; C07D 403/00; C07D 241/04; C07D 295/00
[52] U.S. Cl. ............. 544/121; 544/373; 544/386; 544/366; 514/19
[58] Field of Search ............ 514/12, 21, 19, 514/255, 253, 235.8; 544/121, 373, 386, 366

[56] References Cited

U.S. PATENT DOCUMENTS 3,239,345 3/1966 Hodge et al.
4,036,979 7/1977 Asato .................... 424/275
4,411,890 10/1983 Momany ................ 424/177
5,206,235 4/1993 Fisher et al. ............ 514/213
5,284,841 2/1994 Chu et al. .............. 514/183
5,310,737 5/1994 Fisher et al. ........... 514/215
5,317,017 5/1994 Ok et al. ............... 514/211

FOREIGN PATENT DOCUMENTS

| 0 144 230 A3 | 6/1985 | European Pat. Off. |
| 0 513 974 A1 | 11/1992 | European Pat. Off. |
| WO 94/07486 | 4/1994 | WIPO |
| WO 94/08583 | 4/1994 | WIPO |
| WO 94/13696 | 6/1994 | WIPO |

OTHER PUBLICATIONS

R.G. Smith, et al., *Science*. Reprint Series, 11 Jun. 1993, vol. 260, pp. 1640–1643 "A Nonpeptidyl Growth Hormone Secretagogue".

*Primary Examiner*—Sheela Huff
*Attorney, Agent, or Firm*—J. Eric Thies; David L. Rose

[57] ABSTRACT

Novel piperazine compounds promote the release of growth hormone in humans and animals. This property may be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such piperazine compounds as the active ingredient thereof are also disclosed.

7 Claims, No Drawings

1

PIPERAZINE COMPOUNDS PROMOTE RELEASE OF GROWTH HORMONE

CROSS REFERENCE TO RELATED APPLICATIONS

This application is a national application filed in the United States pursuant to 35 USC § 371, and corresponds to International Application No. PCT/US95/07001, filed Jun. 9, 1995 which is a Continuation of Ser. No. 08/258,644, filed Jun. 13, 1994, now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzo-lactam structure are disclosed in U.S. Pat. No. 4,206,235. The instant compounds are low molecular weight non-peptide analogs for promoting the release of growth hormone which have good stability in a variety of physiological environments and which may be administered parenterally, nasally or by the oral route.

SUMMARY OF THE INVENTION

The instant invention covers certain piperazine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the piperazine compounds. It is a further object of this invention to describe procedures for the preparation of such compounds. A still further object is to describe the use of such compounds to increase the secretion of growth hormone in humans and animals. A still further object of this invention is to describe compositions containing the piperazine compounds for the use of treating humans and animals so as to increase the level of growth hormone secretions. Further objects will become apparent from a reading of the following description.

DESCRIPTION OF THE INVENTION

The novel piperazine compounds of the instant invention are best described in the following structural formula I:

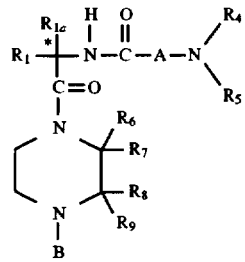

wherein:

$R_1$ is selected from the group consisting of: $C_1$–$C_{10}$ alkyl-, aryl-, aryl($C_1$–$C_6$ alkyl)-, heteroaryl-, heteroaryl($C_1$–$C_6$ alkyl)-, ($C_3$–$C_7$ cycloalkyl)-($C_1$–$C_6$ alkyl)-, ($C_1$–$C_5$ alkyl)-K-($C_1$–$C_5$ alkyl)-, aryl-($C_0$–$C_5$ alkyl)-K-($C_1$–$C_5$ alkyl)-, heteroaryl-($C_0$–$C_5$ alkyl)-K-($C_1$–$C_5$ alkyl)-, and ($C_3$–$C_7$ cycloalkyl)-($C_0$–$C_5$ alkyl)-K-($C_1$–$C_5$ alkyl)-, wherein K is —O—, —S(O)m—, —N($R_2$)C(O)—, —C(O)N($R_2$)—, —OC(O)—, —C(O)O—, —CR$_2$=CR$_2$— or —C≡C—, wherein $R_2$ and the alkyl groups may be further substituted with 1 to 9 halo, —S(O)$_m$R$_{2a}$, 1 to 3 of —OR$_{2a}$, or —C(O)OR$_{2a}$, and wherein aryl is phenyl or naphthyl, and heteroaryl is selected from indolyl, thiophenyl, furanyl, benzothiopheneyl, benzofuranyl, pyridinyl, quinolinyl, triazolyl, imidazolyl, thiazolyl, and benzimidazolyl, wherein aryl and heteroaryl are unsubstituted or substituted with phenyl, phenoxy, halophenyl, 1 to 3 of —C$_1$–C$_6$ alkyl, 1 to 3 of halo, 1 to 2 of —OR$_2$, methylenedioxy, —S(O)$_m$R$_2$, 1 to 2 of —CF$_3$, —OCF$_3$, nitro, —N(R$_2$)(R$_2$), —N(R$_2$)C(O)(R$_2$), —C(O)OR$_2$, —C(O)N(R$_2$)(R$_2$), —SO$_2$N(R$_2$)(R$_2$), —N(R$_2$)SO$_2$-aryl, or —N(R$_2$)SO$_2$R$_2$;

$R_{1a}$ is hydrogen or $C_1$–$C_4$ alkyl;

$R_2$ is selected from the group consisting of: hydrogen, —C$_1$–C$_6$ alkyl, —C$_3$–C$_7$ cycloalkyl, and —CH$_2$-phenyl, wherein the alkyl or the cycloalkyl is unsubstituted or substituted with hydroxyl, $C_1$–$C_3$ alkoxy, thioalkyl, C(O)OR$_{2a}$, and wherein, if two —C$_1$–C$_6$ alkyl groups are present on one atom, the groups may be optionally joined to form a $C_3$–$C_8$ cyclic ring optionally including oxygen, sulfur, or —NR$_{2a}$, the $C_3$–$C_8$ cyclic ring being selected from the group consisting of pyrrolidine, piperidine, piperazine, morpholine, thiomorpholine;

$R_{2a}$ is hydrogen or $C_1$–$C_6$ alkyl;

$R_4$ and $R_5$ are independently selected from the group consisting of: hydrogen, $C_1$–$C_6$ alkyl, substituted $C_1$–$C_6$ alkyl wherein the substituents may be 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, —S(O)$_m$($C_1$–$C_6$ alkyl); or wherein $R_4$ and $R_5$ may be taken together to form —(CH$_2$)$_r$L$_a$(CH$_2$)$_s$—, wherein L$_a$ is —C(R$_2$)$_2$—, —O—, —S(O)$_m$—, or —N(R$_2$)—, wherein r and s are independently 1 to 3, and $R_2$ is as defined above;

$R_6$ and $R_8$ are independently selected from the group consisting of: hydrogen, —$C_1$–$C_{10}$ alkyl, —(CH$_2$)$_q$-aryl, —(CH$_2$)$_q$C(O)OR$_2$, —(CH$_2$)$_q$C(O)N(R$_2$)(R$_2$), —(CH$_2$)$_q$(C$_3$–C$_6$ cycloalkyl), —(CH$_2$)$_q$—K—(C$_1$–C$_6$ alkyl), —(CH$_2$)$_q$—K—(CH$_2$)$_t$-aryl, —(CH$_2$)$_q$—K—(CH$_2$)$_t$—(C$_3$–C$_7$ cycloalkyl), wherein K is —O—, —S(O)$_m$—, —CH=CH—, —C≡C—, —N(R$_2$)C(O)—, —C(O)NR$_2$—, —C(O)O—, or —OC(O)—, wherein the alkyl, —R$_2$, —(CH$_2$)$_q$— and —(CH$_2$)$_t$— groups may be optionally substituted by —C$_1$–C$_4$ alkyl, hydroxyl, —C$_1$–C$_4$ alkoxy, carboxyl or carboxylate-C$_1$–C$_4$ esters, and wherein aryl is phenyl, unsubstituted or substituted with 1 to 3 halo, 1 to 3 —OR$_2$, —C(O)OR$_2$, 1 to 3 —C$_1$–C$_4$ alkyl, —S(O)$_m$R$_2$, or 1H-tetrazol-5-yl;

$R_7$ and $R_9$ are independently selected from the group consisting of: hydrogen, —C$_1$–C$_{10}$ alkyl, —(CH$_2$)$_t$-aryl, wherein aryl is phenyl, unsubstituted or substituted with 1 to 3 halo, 1 to 3 —OR$_2$, —C(O)OR$_2$, 1 to 3 —C$_1$–C$_4$ alkyl, —S(O)$_m$R$_2$, or 1H-tetrazolyl;

A is:

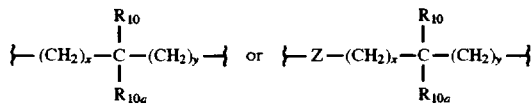

wherein x and y are independently 0, 1, 2 or 3; Z is —N(R$_9$)— or —O—, wherein R$_9$ is hydrogen or C$_1$–C$_6$ alkyl; R$_{10}$ and R$_{10a}$ are independently selected from the group consisting of: hydrogen, —C$_1$–C$_6$ alkyl, trifluoromethyl, phenyl, and substituted C$_1$–C$_6$ alkyl wherein the substituents are selected from the group consisting of: imidazolyl, phenyl, indolyl, p-hydroxyphenyl, —OR$_2$, —S(O)$_m$R$_2$, —C(O)OR$_2$, —C$_3$–C$_7$ cycloalkyl, —N(R$_2$)(R$_2$), and —C(O)N(R$_2$)(R$_2$);

or R$_{10}$ and R$_{10a}$ may independently be joined to one or both of R$_4$ and R$_5$ groups to form alkylene bridges between the terminal nitrogen and the alkyl portion of the R$_{10}$ or R$_{10a}$ groups, wherein the bridge contains 1 to 5 carbons atoms;

B is selected from the group consisting of: phenyl, naphthyl, indolyl, thiophenyl, furanyl, benzothiopheneyl, benzofuranyl, pyridinyl, quinolinyl, triazolyl, imidazolyl, thiazolyl, and benzimidazolyl, which is unsubstituted or substituted with one or more substituents selected from the group consisting of: hydrogen, —C$_1$–C$_6$ alkyl, —(CH$_2$)$_t$—(C$_5$–C$_6$ cycloalkyl), —(CH$_2$)$_t$-aryl, —O—R$_2$, —O—(CH$_2$)$_t$-aryl, —C(O)(CH$_2$)t-aryl, cyano, nitro, halo, —(CH$_2$)$_q$OR$_2$, —(CH$_2$)$_q$CH(OR$_2$)R$_2$, —(CH$_2$)$_q$CH(OR$_2$)—(CH$_2$)$_t$-aryl, —(CH$_2$)$_q$C(O)OR$_2$, —(CH$_2$)$_q$C(O)O(CH$_2$)$_t$-aryl, —(CH$_2$)$_q$C(O)O(CH$_2$)$_t$—(C$_5$–C$_6$ cycloalkyl), —(CH$_2$)$_q$C(O)N(R$_2$)(R$_2$), —(CH$_2$)$_q$C(O)

N(R$_2$)(CH$_2$)$_t$-aryl, —(CH$_2$)$_q$C(O)N(R$_2$)(CH$_2$)$_t$—(C$_5$–C$_6$ cycloalkyl), —(CH$_2$)$_q$N(R$_2$)C(O)(R$_2$), —(CH$_2$)$_q$N(R$_2$)C(O)(CH$_2$)$_t$-aryl, —(CH$_2$)$_q$N(R$_2$)C(O)N(R$_2$)(R$_2$), —(CH$_2$)$_q$N(R$_2$)C(O)N(R$_2$)(CH$_2$)$_t$-aryl, —(CH$_2$)$_q$N(R$_2$)C(O)OR$_2$, —(CH$_2$)$_q$N(R$_2$)C(O)O(CH$_2$)$_t$-aryl, —(CH$_2$)$_q$N(R$_2$)SO$_2$R$_2$, —(CH$_2$)$_q$N(R$_2$)SO$_2$(CH$_2$)$_t$-aryl, —(CH$_2$)$_q$SO$_2$R$_2$, —(CH$_2$)$_q$SO$_2$(CH$_2$)$_t$-aryl, —(CH$_2$)$_q$SO$_2$N(R$_2$)(R$_2$), —(CH$_2$)$_q$SO$_2$N(R$_2$)(CH$_2$)$_t$-aryl, —(CH$_2$)$_q$SO$_2$N(R$_2$)C(O)R$_2$, —(CH$_2$)$_q$ SO$_2$N(R$_2$)C(O)-aryl, —(CH$_2$)$_q$C(O)NHSO$_2$R$_2$, —(CH$_2$)$_q$(1H-tetrazol-5-yl), —(CH$_2$)$_q$(imidazol-2-yl), —(CH$_2$)$_q$(1,2,4-triazol-1-yl), —(CH$_2$)$_q$CONH(1H-tetrazol-5-yl), —CH$_2$)$_q$CONH(imidazol-2-yl), and —(CH$_2$)$_q$CONH(1,2,4-triazol-1-yl), wherein aryl is phenyl unsubstituted or substituted with 1 to 2 halo, amino, 1 to 2 —OR$_2$, or 1 to 2 —(C$_1$–C$_4$ alkyl);

m is 0, 1, or 2;

n is 1 or 2;

q is 0, 1, 2, 3 or 4;

t is 0, 1, 2 or 3;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halo" or "halogen" is intended to include the halogen atoms fluorine, chlorine, bromine and iodine.

The term "aryl" (unless otherwise specified) is intended to include phenyl and naphthyl. The term "heteroaryl" (unless otherwise specified) is intended to include aromatic residues of 5- and 6- membered rings with 1 to 3 heteroatoms or fused 5- or 6-membered bicyclic rings with 1 to 4 heteroatoms of nitrogen, sulfur or oxygen. Examples of such heteroaryl include indolyl, dihydroindolyl, thiophenyl, furanyl, benzothiopheneyl, benzofuranyl, pyridinyl, pyrimidinyl, quinolinyl, triazolyl, imidazolyl, thiazolyl, tetrazolyl, and benzimidazolyl.

Certain of the above defined terms may occur more than once in the above formula and upon such occurrence each term shall be defined independently of the other, i.e. when any variable (e.g., alkyl, aryl, R$_2$, etc.) occurs more than one time within any variable or in Formula I, its definition on each occurrence is independent of its definition at every other occurrence.

Preferred compounds of the instant invention include those of structural formula I wherein:

R$_1$ is selected from the group consisting of: C$_1$–C$_{10}$ alkyl, aryl(C$_1$–C$_4$ alkyl)-, C$_5$–C$_6$ cycloalkyl-(C$_1$–C$_4$ alkyl)-, (C$_1$–C$_4$ alkyl)-K—C$_1$–C$_2$ alkyl-, aryl(C$_0$–C$_2$ alkyl)-K—(C$_1$–C$_2$ alkyl)-, C$_3$–C$_6$cycloalkyl(C$_0$–C$_2$alkyl)-K—(C$_1$–C$_2$alkyl)-, wherein K is O or S(O)$_m$, and the aryl is phenyl, unsubstituted or substituted by 1 to 2

—$C_1$–$C_4$ alkyl, 1 to 2 halo, —$OR_2$, —$C(O)OR_2$, —$CF_3$ or —$S(O)_mR_2$;

$R_2$ is selected from the group consisting of: hydrogen, $C_1$–$C_6$ alkyl, $C_3$–$C_6$ cycloalkyl, wherein the alkyl or the cycloalkyl is unsubstituted or substituted with hydroxyl, $C_1$–$C_3$ alkoxy, thioalkyl, $C(O)OR_{2a}$, and, if two $C_1$–$C_6$ alkyls are present on one atom, they may be optionally joined to form a $C_5$–$C_6$ cyclic ring optionally including the heteroatoms oxygen or $NR_{2a}$, the $C_3$–$C_8$ cyclic ring being selected from the group consisting of pyrrolidine, piperidine, piperazine, morpholine, thiomorpholine;

$R_{2a}$ is hydrogen or $C_1$–$C_4$ alkyl;

$R_4$ and $R_5$ are independently selected from the group consisting of: hydrogen, $C_1$–$C_4$ alkyl, substituted $C_1$–$C_4$ alkyl wherein the substituents may be 1 to 2 hydroxy or $S(O)_m(C_1$–$C_3$alkyl);

$R_6$ and $R_8$ are independently selected from the group consisting of: hydrogen, —$C_1$–$C_{10}$ alkyl, —$(CH_2)_t$-aryl, —$(CH_2)_qC(O)OR_2$, —$(CH_2)_qC(O)N(R_2)(R_2)$, —$(CH_2)_q(C_3$–$C_6$ cycloalkyl), —$(CH_2)_n$—K—$(C_1$–$C_6$ alkyl), —$(CH_2)_n$—K—$(CH_2)_t$-aryl, —$(CH_2)_n$—K—$(CH_2)_t$—$(C_3$–$C_7$ cycloalkyl), wherein K is —O—, —$S(O)_m$—, —$N(R_2)C(O)$—, —$C(O)NR_2$—, —$C(O)O$—, or —$OC(O)$—, wherein the alkyl, —$R_2$, —$(CH_2)_q$— and —$(CH_2)_t$— groups may be optionally substituted by —$C_1$–$C_4$ alkyl, hydroxyl, —$C_1$–$C_4$ alkoxy, carboxyl or carboxylate-$C_1$–$C_4$ esters, and wherein aryl is phenyl, unsubstituted or substituted with 1 to 3 halo, 1 to 3 —$OR_2$, —$C(O)OR_2$, 1 to 3 —$C_1$–$C_4$ alkyl, —$S(O)_mR_2$, or 1 H-tetrazolyl;

$R_7$ and $R_9$ are independently selected from the group consisting of: hydrogen, —$C_1$–$C_{10}$ alkyl, —$(CH_2)_t$-aryl, wherein the aryl group may be optionally substituted with 1 to 3 halo, 1 to 3 —$OR_2$, —$C(O)OR_2$, 1 to 3 —$C_1$–$C_4$ alkyl, —$S(O)_mR_2$ or 1H-tetrazol-5-yl;

A is:

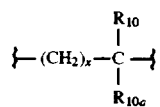

wherein x is 0 or 1;

$R_{10}$ and $R_{10a}$ are independently selected from the group consisting of: hydrogen, and $C_1$–$C_3$ alkyl; or $R_{10}$ and $R_{10a}$ can independently be joined to one or both of the $R_4$ and $R_5$ groups to form alkylene bridges between the terminal nitrogen and the alkyl portion of the $R_{10}$ or $R_{10a}$ groups to form 5 or 6 membered rings containing the terminal nitrogen;

B is selected from the group consisting of: phenyl, indolyl, pyridinyl, and pyrimidinyl, unsubstituted or substituted with one or more substituents selected from the group consisting of: hydrogen, —$C_1$–$C_6$ alkyl, —$(CH_2)_t$—$(C_5$–$C_6$ cycloalkyl), —$(CH_2)_t$-aryl, —O—$R_2$, —O—$(CH_2)_t$-aryl,—$C(O)(CH_2)_t$-aryl, cyano, nitro, halo, —$(CH_2)_qOR_2$, —$(CH_2)_qCH(OR_2)$ $R_2$, —$(CH_2)_qCH(OR_2)$—$(CH_2)_t$-aryl, —$(CH_2)_qC(O)$ $OR_2$, —$(CH_2)_qC(O)O(CH_2)_t$-aryl, —$(CH_2)_qC(O)O$ $(CH_2)_t$—$(C_5$–$C_6$ cycloalkyl), —$(CH_2)_qC(O)N(R_2)$ $(R_2)$, —$(CH_2)_qC(O)N(R_2)(CH_2)_t$-aryl, —$(CH_2)_qC(O)$ $N(R_2)(CH_2)_t$–$(C_5$–$C_6$ cycloalkyl), —$(CH_2)_qN(R_2)C(O)$ $(R_2)$, —$(CH_2)_qN(R_2)C(O)(CH_2)_t$-aryl, —$(CH_2)_qN(R_2)$ $C(O)N(R_2)(R_2)$, —$(CH_2)_qN(R_2)C(O)N(R_2)(CH_2)_t$-aryl, —$(CH_2)_qN(R_2)C(O)OR_2$, —$(CH_2)_qN(R_2)C(O)O$ $(CH_2)_t$-aryl, —$(CH_2)_qN(R_2)SO_2R_2$, —$(CH_2)_qN(R_2)$ $SO_2(CH_2)_t$-aryl, —$(CH_2)_qSO_2R_2$, —$(CH_2)_qSO_2$ $(CH_2)_t$- aryl, —$(CH_2)_qSO_2N(R_2)(R_2)$, —$(CH_2)_qSO_2N$ $(R_2)(CH_2)_t$-aryl, —$(CH_2)_qSO_2N(R_2)C(O)R_2$, —$(CH_2)_q$ $SO_2N(R_2)C(O)$-aryl, —$(CH_2)_qC(O)$ $NHSO_2R_2$, —$(CH_2)_q(1H$-tetrazol-5-yl), —$(CH_2)_q$ (imidazol-2-yl), —$(CH_2)_q(1,2,4$-triazol- 1 -yl), —$(CH_2)_qCONH(1H$-tetrazol-5-yl), —$(CH_2)_qCONH$ (imidazol-2-yl), and —$(CH_2)_qCONH(1,2,4$-triazol-1-yl), wherein aryl is phenyl, unsubstituted or substituted with 1 to 2 halo, amino, 1 to 2 —$OR_2$, or 1 to 2 -($C_1$–$C_4$ alkyl), m is 0, 1 or 2;

n is 1 or 2;

q is 0, 1, 2 or 3;

t is 0, 1, 2 or 3;

and pharmaceutically acceptable salts and individual diastereomers thereof.

Most preferred compounds of the instant invention are realized in structural formula V:

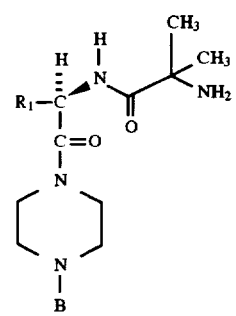

wherein $R_1$ is selected from the group consisting of:

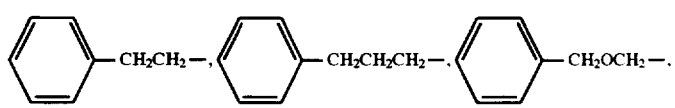

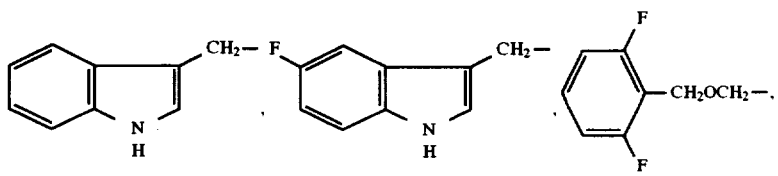

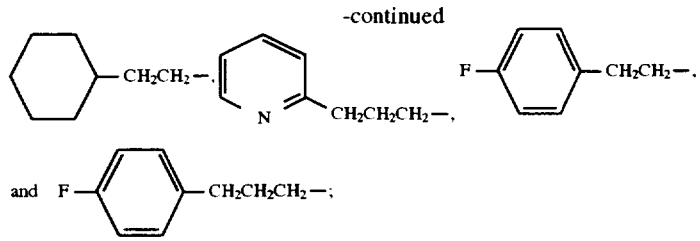

B is phenyl unsubstituted or substituted with one or more substituents selected from the group consisting of: hydrogen, —$(CH_2)_t$-aryl, $C_1$–$C_3$ alkyl, —$(CH_2)_q OR_2$, —$(CH_2)_q C(O)OR_2$, —$(CH_2)_q C(O)O(CH_2)_t$-aryl, —$(CH_2)_q C(O)N(R_2)(R_2)$, —$(CH_2)_q C(O)N(R_2)(R_2)$, —$(CH_2)_q C(O)N(R_2)(CH_2)_t$-aryl, —$(CH_2)_q N(R_2)C(O)(R_2)$, —$(CH_2)_q N(R_2)C(O)N(R_2)(R_2)$, —$(CH_2)_q N(R_2)C(O)OR_2$, —$(CH_2)_q N(R_2)SO_2R_2$, —$(CH_2)_q N(R_2)SO_2(CH_2)_t$-aryl, —$(CH_2)_q SO_2R_2$, —$(CH_2)_q SO_2(CH_2)_t$-aryl, —$(CH_2)_q SO_2N(R_2)(R_2)$, —$(CH_2)_q SO_2N(R_2)(CH_2)_t$-aryl, —$(CH_2)_q SO_2N(R_2)C(O)R_2$, —$(CH_2)_q SO_2N(R_2)C(O)$-aryl, —$(CH_2)_q C(O)NHSO_2R_2$, —$(CH_2)_q$(1H-tetrazol-5-yl), —$(CH_2)_q$(imidazol-2-yl), —$(CH_2)_q$(1,2,4-triazol-1-yl), —$(CH_2)_q$CONH(1H-tetrazol-5-yl), —$(CH_2)_q$CONH(imidazol-2-yl), and —$(CH_2)_q$CONH(1,2,4-triazol-1-yl), wherein aryl is phenyl unsubstituted or substituted with 1to 2 halo, amino, 1 to 2 —$OR_2$, or 1 to 2 —($C_1$–$C_4$ alkyl);

$R_2$ is selected from the group consisting of: hydrogen, —$C_1$–$C_6$ alkyl, —$C_3$–$C_7$ cycloalkyl, and —$CH_2$-phenyl, optionally substituted with hydroxyl, $C_1$–$C_3$-alkoxy, thiomethyl, —$C(O)OR_{2a}$, wherein if two —$C_1$–$C_6$ alkyl groups are present on one atom, the groups may be optionally joined to form a $C_3$–$C_4$ cyclic ring optionally including oxygen, sulfur or —$NR_{2a}$;

$R_{2a}$ is hydrogen or $C_1$–$C_6$ alkyl;

q is 0, 1, 2 or 3;

t is 0, 1, or 2;

and the pharmaceutically acceptable salts and individual diastereomers thereof.

Representative most preferred growth hormone releasing compounds of the present invention include the following:

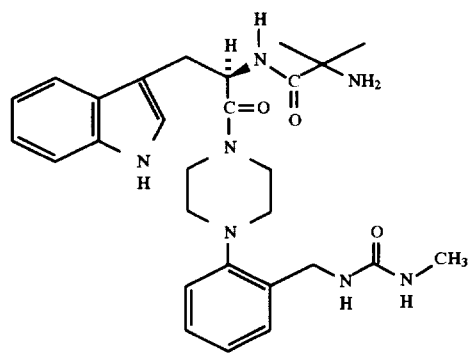

1)

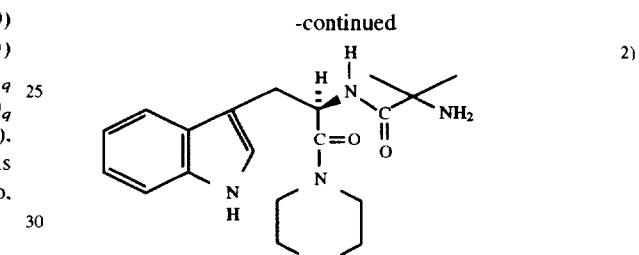

2)

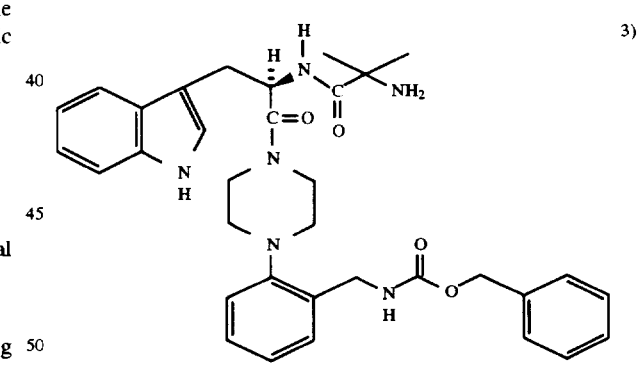

3)

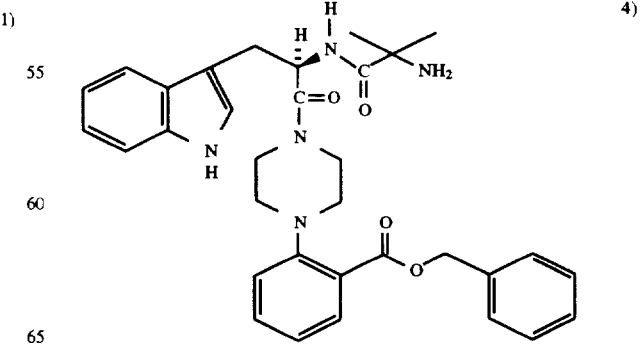

4)

9
-continued
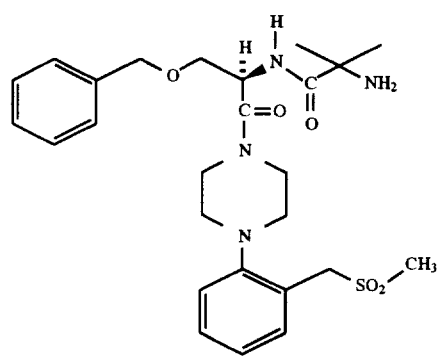
5)
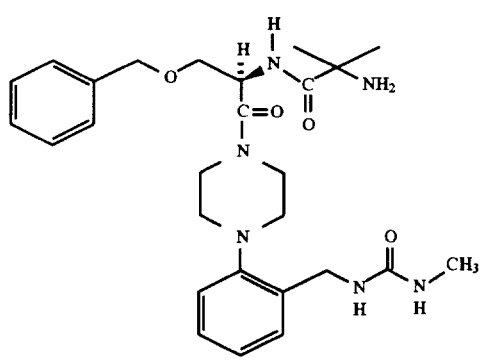
6)
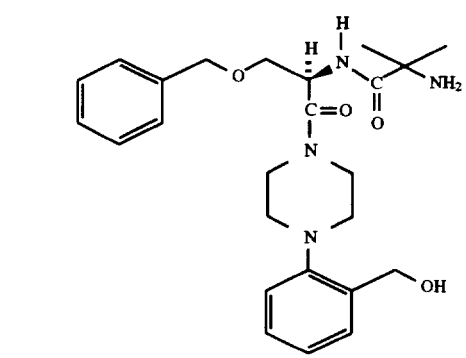
7)
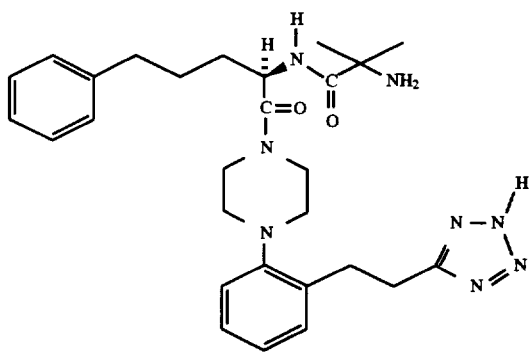
8)
10
-continued
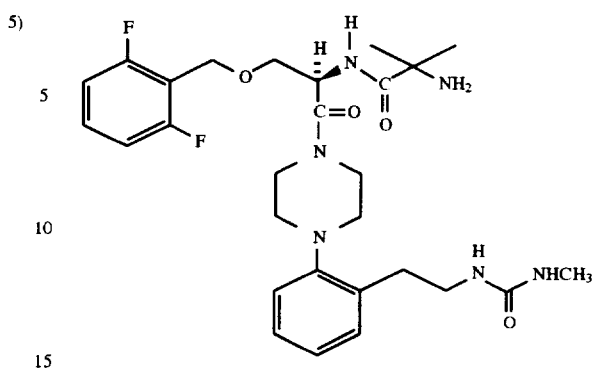
9)
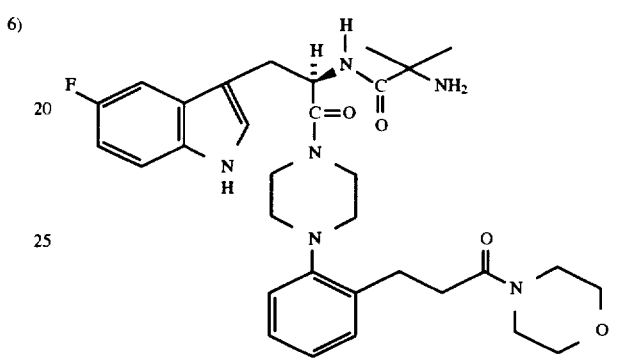
10)
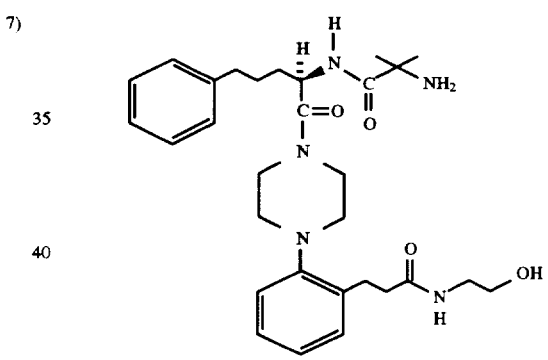
11)
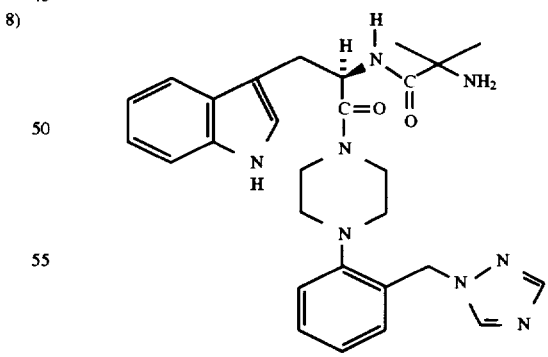
12)

13)

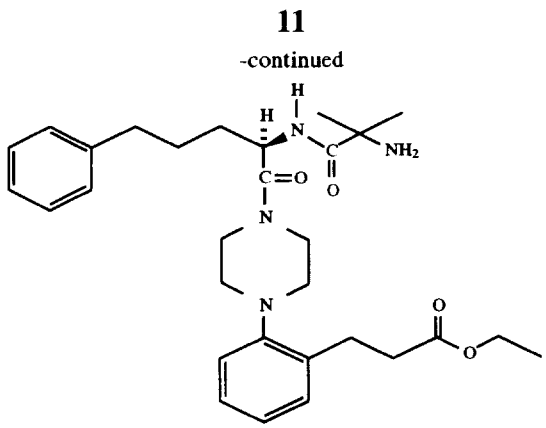

14)

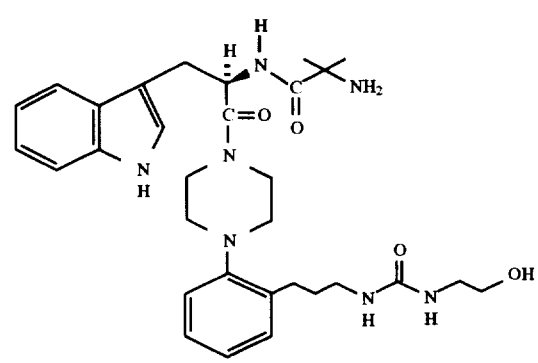

15)

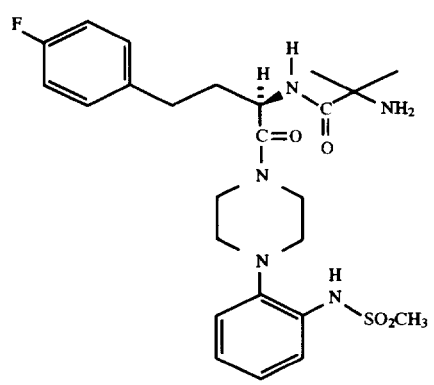

16)

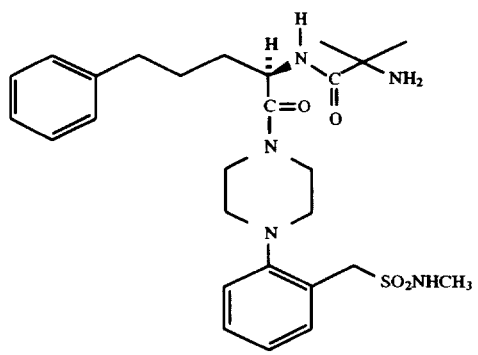

17)

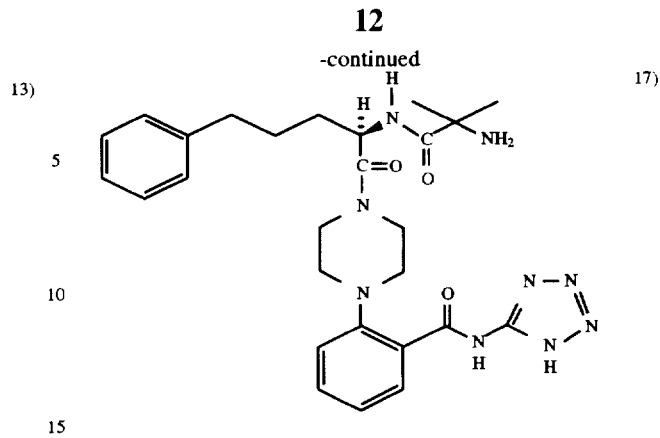

and the pharmaceutically acceptable salts thereof.

Throughout the instant application, the following abbreviations are used with the following meanings:

| | |
|---|---|
| BOC | t-butyloxycarbonyl |
| BOP | Benzotriazol-1-yloxy tris(dimethylamino)-phosphonium hexafluorophosphate |
| CBZ | Benzyloxycarbonyl |
| DIBAL-H | diisobutylaluminum hydride |
| DMF | N,N-dimethylformamide |
| EDC | 1-(3-dimethylaminopropyl)-3-ethylcarbodiimide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In the case of the asymmetric center represented by the asterisk in Formula I, it has been found that the absolute stereochemistry of the more active and thus more preferred isomer is as shown in Formula Ia. With the $R_{1a}$ substituent as hydrogen, the special configuration of the asymmetric center corresponds to that in a D-amino acid. In most cases this is also designated an R-configuration although this will vary according to the values of $R_1$ and $R_{1a}$ used in making R- or S- stereochemical assignments.

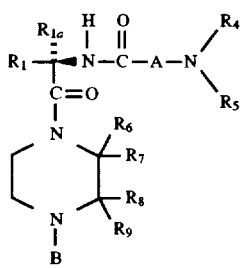

Formula Ia

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy may be isolated in the form of their inorganic salt in which the counterion may be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes.

The phrase standard peptide coupling reaction conditions is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize the undesired reaction are well documented. Conditions required to remove protecting groups which may be present and can be found in Greene, T; Wuts, P. G. M. *Protective Groups in Organic Synthesis*, John Wiley & Sons, Inc., New York, N.Y. 1991. CBZ and BOC were used extensively in the synthesis, and their removal conditions are known to those skilled in the art. Removal of CBZ groups may be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups may also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 may be prepared by literature methods (Williams, R. M. *Synthesis of Optically Active α-Amino Acids*, Pergamon Press: Oxford, 1989). Many of the piperazines of formula 2 are either commercially available or known in the literature and others may be prepared following literature methods desribed for known compounds, some of which are described here. The skills required in carrying out the reaction and purification of the resulting reaction products are known to those in the art. Purification procedures includes crystallization, normal phase or reverse phase chromatography.

REACTION SCHEME 1

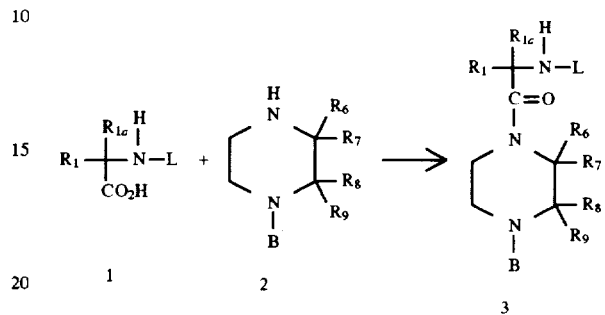

Intermediates of formula 3 may be synthesized as described in Reaction Scheme 1. Coupling of amine of formula 2, whose preparation is described later (if not commercially available), to protected amino acids of formula 1, wherein L is a suitable protecting group, may be conveniently carried out employing standard peptide coupling conditions.

REACTION SCHEME 2

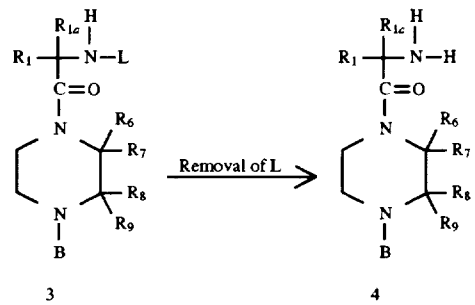

Conversion of 3 to intermediate 4 may be carried out as illustrated in Reaction Scheme 2 by removal of the protecting group L (CBZ, BOC, etc.) by methodology well known in the art.

REACTION SCHEME 3

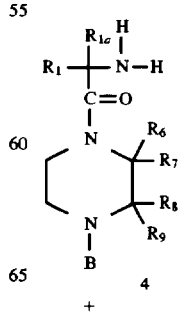

+

-continued
REACTION SCHEME 3

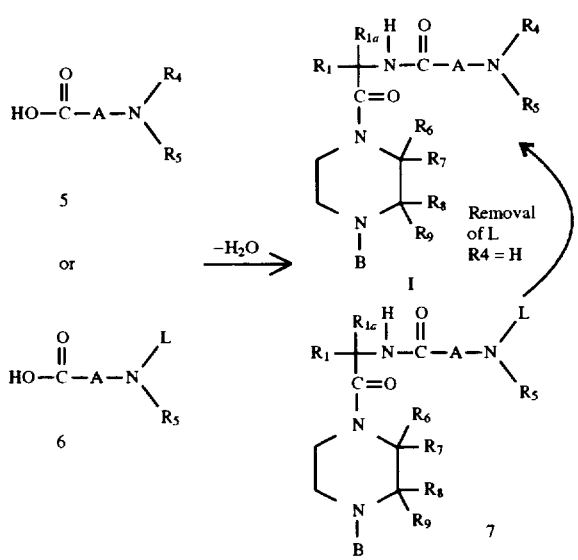

Intermediates of formula 5, wherein A is connected to the carboxyl by a carbon atom (i.e. A is —(CH$_2$)$_x$—C(R$_{10}$)(R$_{10a}$)—(CH$_2$)$_y$—) may be prepared as shown in Reaction Scheme 3 by coupling intermediates of formula 4 to amino acids of formula 5 under the standard peptide coupling reaction conditions. The amino acids 5, as amino acid 1, are either commercially available or may be synthesized. Also if R$_4$ or R$_5$ is a hydrogen then the protected amino acids 6 are employed in the coupling reaction, wherein L is a protecting group as defined above. The removal of L in 7 to afford I, where R$_4$=H, may be carried out under conditions known in the art.

REACTION SCHEME 4

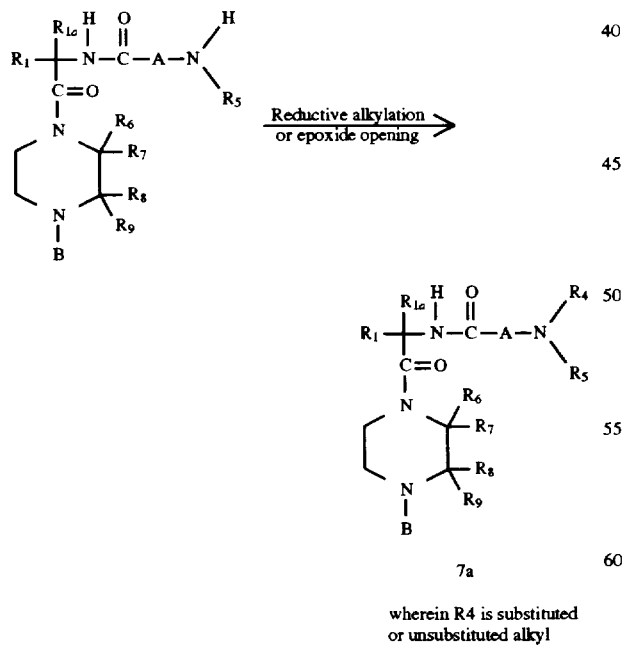

wherein R4 is substituted or unsubstituted alkyl

Compounds of formula I wherein R$_4$ and/or R$_5$ is a hydrogen may be further elaborated to new compounds 7a with preferred side chains R$_4$=CH$_2$—CH(OH)—CH$_2$X, wherein X=H or OH) which are substituted on the amino group as depicted in Reaction Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation may be accomplished via an epoxide opening reaction.

REACTION SCHEME 5

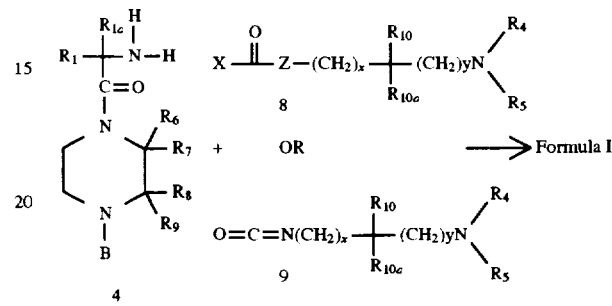

Compounds of formula I, wherein A is Z—(CH$_2$)$_x$—C (R$_{10}$)(R$_{10a}$)—(CH$_2$)$_y$ and Z is N—R$_6$ or O may be prepared as shown in Reaction Scheme 5 by reacting 4 with reagents 8, wherein X is a good leaving group such as Cl, Br, I, or imidazole. Alternatively, 4 may be reacted with an isocyanate of formula 9 in an inert solvent such as 1,2-dichloroethane to provide compounds of formula I where Z is NH.

The compounds of general formula I of the present invention may also be prepared in a convergent manner as described in reaction Reaction Schemes 6, 7 and 8.

REACTION SCHEME 6

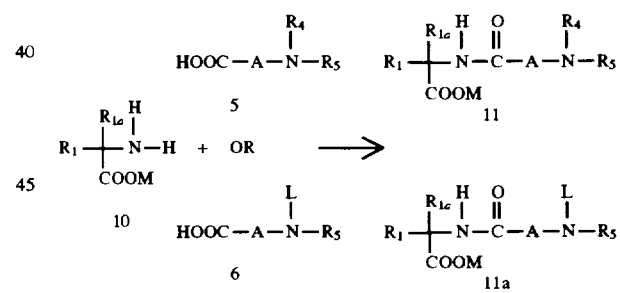

The carboxylic acid protected amino acid derivatives 10 are, in many cases, commercially available where M=methyl, ethyl, or benzyl esters. Other ester protected amino acids may be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions include the reaction of a protected amino acid with a diazoalkane, or with an alcohol and an acid activating agent such as EDC, DCC in the presence of a catalyst such as DMAP and removal of the protecting group L.

Intermediates of formula 11 or 11a, may be prepared as shown in Reaction Scheme 6 by coupling of amino acid ester 10 to amino acids of formula 6 or 7. When a urea linkage is present in 11 or 11a, it may be introduced as illustrated in Reaction Scheme 5.

REACTION SCHEME 7

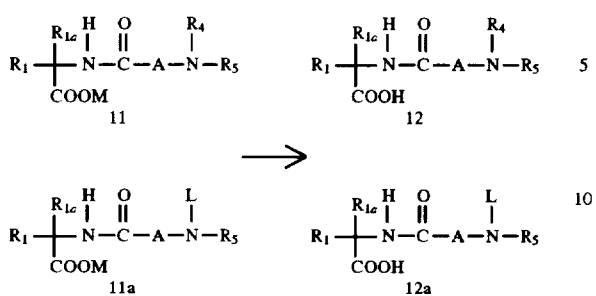

Conversion of the ester 11 or 11a to intermediate acids 12 or 12a may be achieved by a number of methods known in the art as described in Reaction Scheme 7. For example, methyl and ethyl esters may be hydrolyzed with lithium hydroxide in a protic solvent like aqueous methanol. In addition, removal of benzyl group may be accomplished by a number of reductive methods including hydrogenation in the presence of palladium catalyst in a protic solvent such as methanol. An allyl ester may be cleaved with tetrakis-triphenylphosphine palladium catalyst in the presence of 2-ethylhexanoic acid in a variety of solvents including ethyl acetate and dichloromethane (see *J. Org. Chem.* 1982, 42, 587).

REACTION SCHEME 8

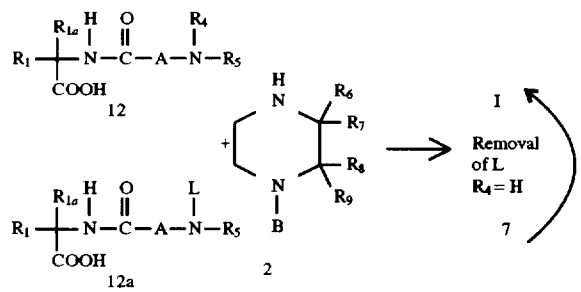

Acid 12 or 12a may then be elaborated to I or compound 7 as described in Reaction Scheme 8. Coupling of piperazines of formula 2 to acids of formula 12 or 12a, wherein L is a suitable protecting group, is conveniently carried out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Reaction Scheme 4.

The substituted piperazines are either commercially available or may be prepared by literature procedures. Illustrated here are some, but by no means all, the methods for their preparation. Other methods will be readily apparent to one skilled in the art from the disclosure herein.

The carboxylic acid functionality at the 2-position of these compounds may be converted to ester, amide, acyl sulfonamide, and moieties according to the conventional methods well documented in the literature and known to those skilled in the art (*The Practice of Peptide Synthesis*, by M. Bodanszky and A. Bodanszky, Springer-Verlag, 1984). L is an appropriate protecting group such as BOC, CBZ, etc. The carboxylic acid may also be converted into its next higher homologue, or to a derivative of the homologous acid, such as amide or ester by an Arndt-Eistert reaction. Alternatively, the ester may be directly homologated by the protocol using enolate anions described by C. J. Kowalski and R. E. Reddy in *J. Org. Chem.*, 57, 7194–7208 (1992). The resulting acid and/or ester may be converted to the next higher homologue, and so on and so forth.

REACTION SCHEME 9

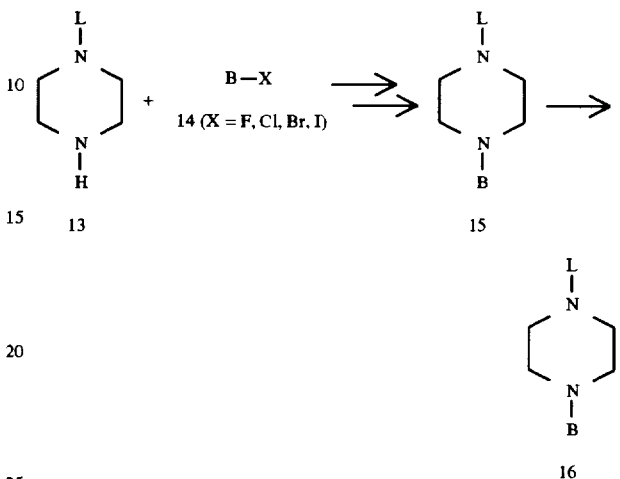

The synthesis of substituted aryl and heteroaryl piperazines has been detailed in a number of research articles. One of the standard approaches to the synthesis of aryl and heteroaryl piperazines involves a nucleophilic aromatic substitution reaction as shown in Scheme 9. The reaction of a protected piperazine of formula 13 (L=BOC, CBZ, etc.) with a halo-aromatic reactant of formula 14 (B–X: wherein X=Cl, F, Br, or I; usually F) in the presence of a base and/or Cu gives substituted piperazines 15 (L=BOC, CBZ, etc.). Removal of the protecting group L can be accomplished by methods familiar to those skilled in the art. These deblocked piperazines may be readily elaborated to the growth hormone secretagogues of formula I employing methodology detailed in Schemes 1–8.

REACTION SCHEME 10

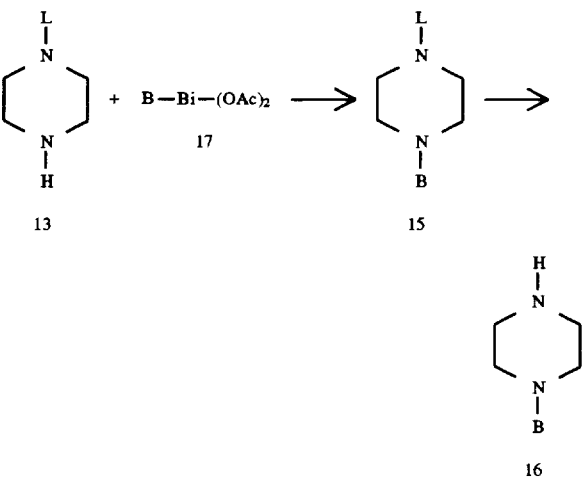

Other methods that may be employed to prepare aryl and heteroaryl piperazines include the copper catalyzed N-arylation of amines by triarylbismuth diacetates (D. H. R. Barton, et al., *Tetrahedrony Lett.* 1986, 27, 3615–3618) as shown in Scheme 10.

REACTION SCHEME 11

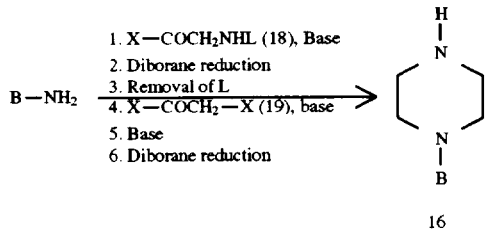

1. X—COCH₂NHL (18), Base
2. Diborane reduction
3. Removal of L
4. X—COCH₂—X (19), base
5. Base
6. Diborane reduction Another method that has been employed to synthesize aryl piperazines involves the elaboration of the piperazine unit from anilines via a multistep sequence as shown in Scheme 11.

Substituted piperazines may be prepared in optically active form by the methods of Ashton, et al., (PCT Patent Publication WO 92/20661; U.S. Pat. No. 5,292,726). Substituted pyrazines are first reduced to substituted piperazines by standard methods including hydrogenation with Pd/C in aqueous alkali. Separation of the enantiomers is carried out by classical resolution with recrystallization of the salt derived from an optically acid like camphor sulfonic acid.

REACTION SCHEME 12

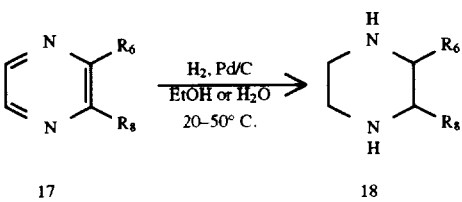

For the synthesis of compounds of formula I, the piperazine nucleus may be constructed by various methods. One such useful method, shown in Scheme 12, entails catalytic hydrogenation of a substituted pyrazine 17 to give the piperazine 18 (E. Felder, et al., *Helv. Chim. Acta*, 43, 888 (1960)). This is typically accomplished by use of palladium on carbon as the catalyst, in a solvent such as ethanol or water, at a temperature of 20–50° C.

REACTION SCHEME 13

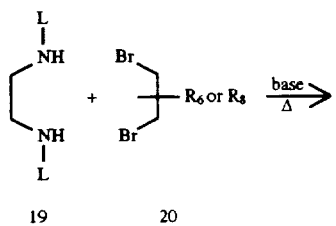

-continued
REACTION SCHEME 13

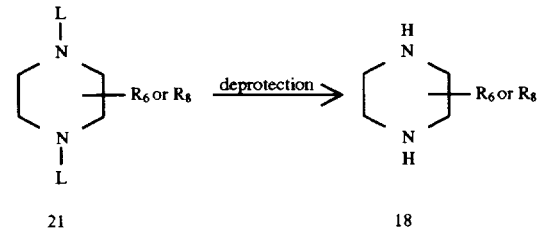

Another method (Scheme 13) involves reaction of a protected diamine 19 with a dibromo compound 20 in the presence of base at elevated temperature to give the bis-protected piperazine 21, which yields 18 upon deprotection. This method has been particularly useful in cases where 20 is a 2,3-dibromo ester. In the variation used by Piper, et al., (J. R. Piper, L. M. Rose, and T. P. Johnston, *J. Org. Chem.*, 37, 4476 (1972)), the protecting group L is p-toluenesulfonyl, and the disodium salt of 19 is heated with 20 ($R_6$ or $R_8$=CO₂Et) in DMF at up to about 100°–110° C. to form the piperazine 21. The p-toluenesulfonyl protecting groups can be removed (along with simultaneous ester hydrolysis) by heating 21 at reflux in 48% HBr (F. L. Bach, Jr., et al., *J. Am. Chem. Soc.*, 77, 6049 (1955)). In another variation (E. Jucker and E. Rissi, *Helv. Chim. Acta*, 45, 2383 (1962)), the protecting group L is benzyl, and heating 19 with 20 ($R_6$ or $R_8$=CO₂Et) in benzene yields 21. In this case deprotection is achieved (without ester hydrolysis) by palladium-catalyzed hydrogenation in acetic acid.

REACTION SCHEME 14

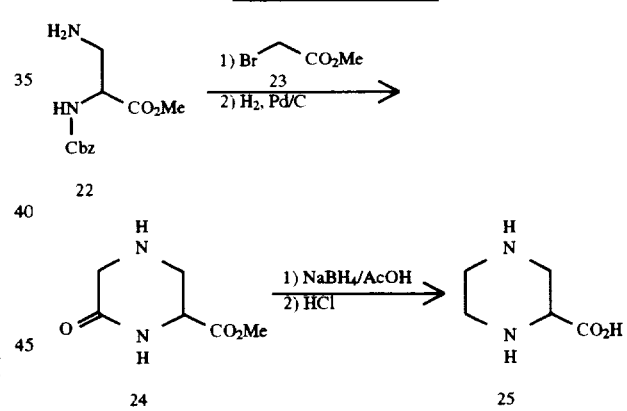

Another route to piperazine-2-carboxylic acids is illustrated in Scheme 14. The a-Cbz-protected a,b-diamino ester 22 is reacted with a-bromo ester 23. Following hydrogenolyis of the Cbz group, the oxopiperazinecarboxylate 24 is obtained. Selective reduction and hydrolysis affords the piperazinecarboxylic acid 25. This route (B. Aebischer, et al., *Helv. Chim. Acta*, 72, 1043 (1989)) has been used to prepare chiral piperazine-2-carboxylic acid from a chiral diamino ester 22. Optically active piperazine-2-carboxylic acids have also been obtained from the racemate via a camphorsulfonic acid salt (E. Felder, *Helv. Chim Acta*, 43, 888 (1960)) or menthyl ester (B. Aebischer, et al., *Helv. Chim. Acta*, 72, 1043 (1989)).

REACTION SCHEME 15
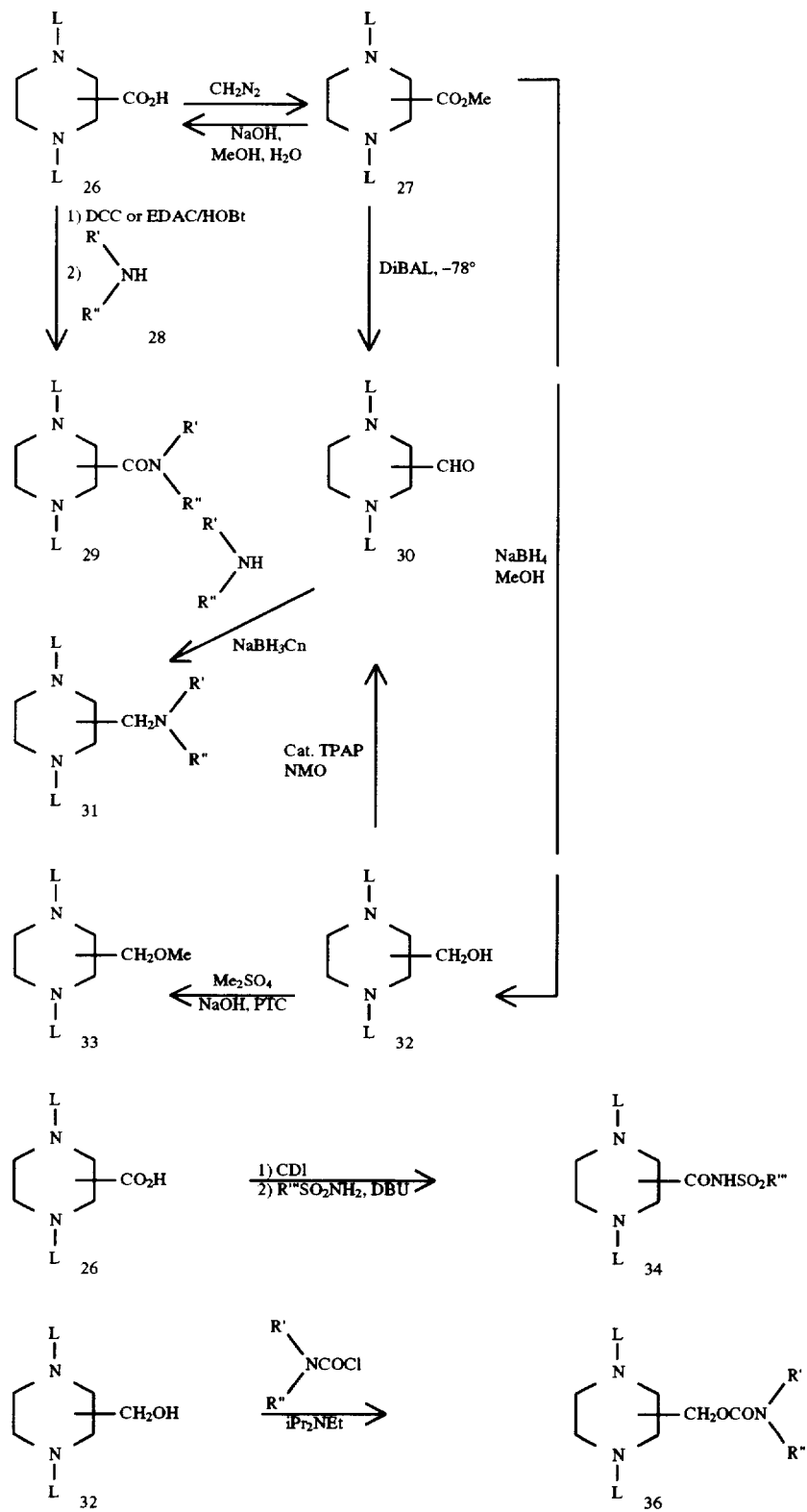

-continued
REACTION SCHEME 15

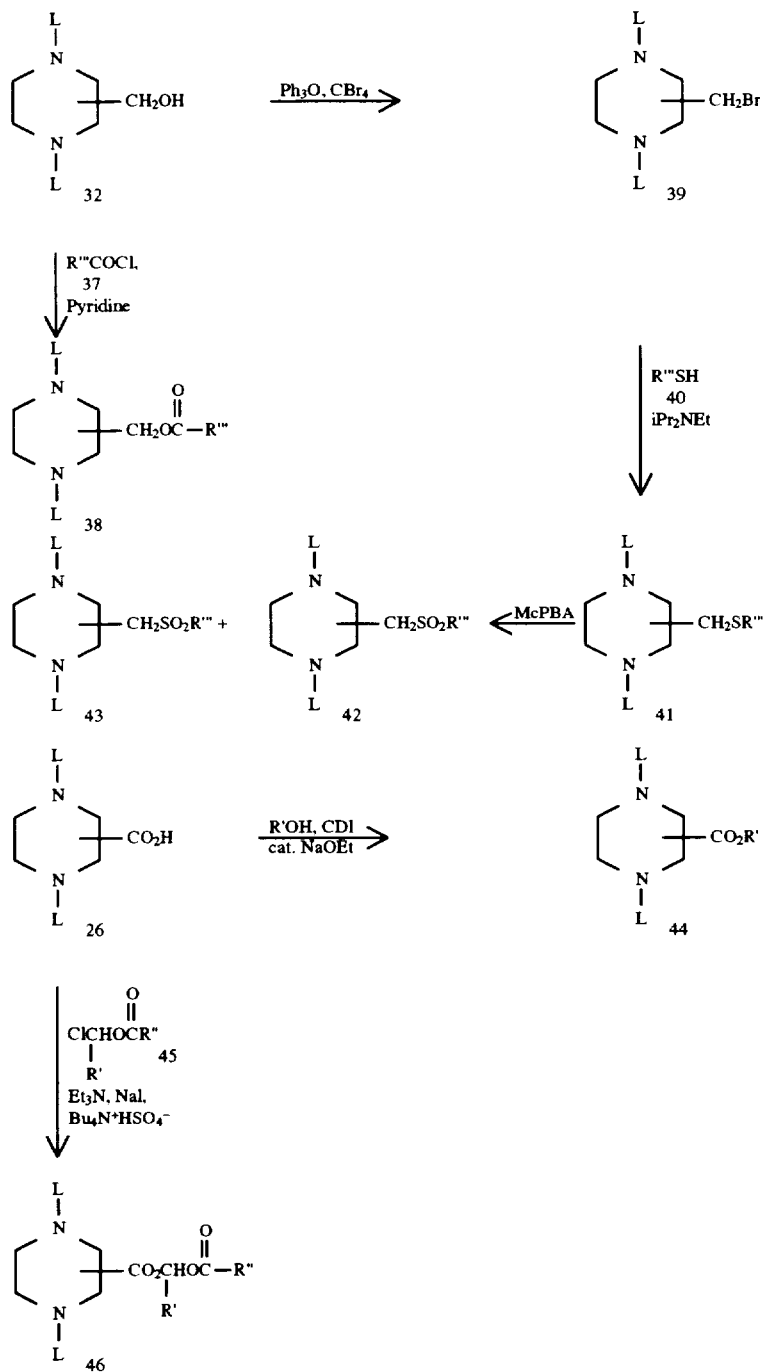

In compounds of formula I, the $R_6$, $R_7$, $R_8$ and $R_9$ substituents may be present at the time the piperazine ring system is formed, as shown in Schemes 9–14. However, additional transformations may be carried out on the $R_6$, $R_7$, $R_8$ and/or $R_9$ functional groups after elaboration of the diacylated (or carbamoylated, etc.) piperazine, as shown in Scheme 15. For example, piperazinecarboxylic acid 26 may be readily converted to its methyl ester 27 by treatment with diazomethane, preferably in ether-methanol or THF at 0°–25° C. (B. Aebischer, et al., Helv. Chim. Acta, 72, 1043 (1989); C. F. Bigge, et al., Tetrahedron Lett., 30, 5193 (1990)) or by other methods (C. F. Bigge, et al., op. cit.). The acid 26 may also be obtained by saponification of 27 under standard conditions. The methyl ester 27 may also be reduced to alcohol 32 by treatment with sodium borohydride/methanol according to the procedures of Sugihara and Nishikawa (EPO Patent Publication EP 0.368.670). Treatment of carboxylic acid 26 with DCC or EDAC/HOBt followed by amine 28 affords the amide 29. Methyl ester 27 may be transformed to aldehyde 30 by use of diisobutylaluminum hydride under controlled conditions at -78° C. Alternatively, alcohol 32 can be oxidized to 30 by various methods, such as the use of catalytic tetrapropylammonium perruthenate (TPAP) and 4-methylmorpholine N-oxide (NMO) in the presence of molecular sieves (W. P. Griffith, et al., *J. Chem. Soc. Chem Commun.*, 1625 (1987)). Using standard reductive alkylation conditions, 30 is reacted with amine 28 in the presence of sodium cyanoborohydride to give the aminomethylpiperazine 31. Alcohol 32 may be converted to methyl ether 33 by use of dimethyl sulfate, 50% aqueous sodium hydroxide, and a phase transfer catalyst (PTC) such as tetrabutylammonium hydrogen sulfate (A. Merz, *Angew. Chem. Int. Ed. Engl.*, 12, 846 (1973)).

The acylsulfonamide derivative 34 is obtained by treating the carboxylic acid 26 with carbonyldiimidazole and then with the sulfonamide, R'''SO$_2$NH$_2$, and DBU as base in a solvent such as THF. Treatment of alcohol 32 with the carbamoyl chloride 35 in the presence of a base such as N,N-diisopropylethylamine yields the carbamate 36.

Similarly, reaction of 32 with acid chloride 37 in the presence of a base like pyridine gives the acyloxymethylpiperazine 38. The bromomethyl intermediate 39 is available by treatment of alcohol 32 with triphenylphosphine and carbon tetrabromide. Displacement of the bromo group by a thiol 40 occurs in the presence of N,N-diisopropylethylamine as base to give the thioether 41. Oxidation of 41 to the sulfoxide 42 or the sulfone 43 may be carried out with m-chloroperbenzoic acid (MCPBA) in a solvent such as methylene chloride or acetic acid. Whether 42 or 43 is the major or exclusive product is dependent on the stoichiometry, reaction time, and temperature.

In addition to the methyl ester 27, the carboxylic acid 26 may be converted into other esters 44, for example by treatment with carbonyldiimidazole and an alcohol, ROH, in the presence of catalytic sodium ethoxide (H. A. Staab and A. Mannschreck, *Chem. Ber.*, 95, 1284 (1962)). An a-(acyloxy)alkyl ester 46 may be obtained by reaction of 25 with an a-chloralyl ester 45 in the presence of triethylamine, sodium iodide, and tetrabutylammonium hydrogen sulfate as phase transfer catalyst (E. W. Petrillo, et al., U.S. Pat. No. 4,873,356 (1989)).

REACTION SCHEME 16

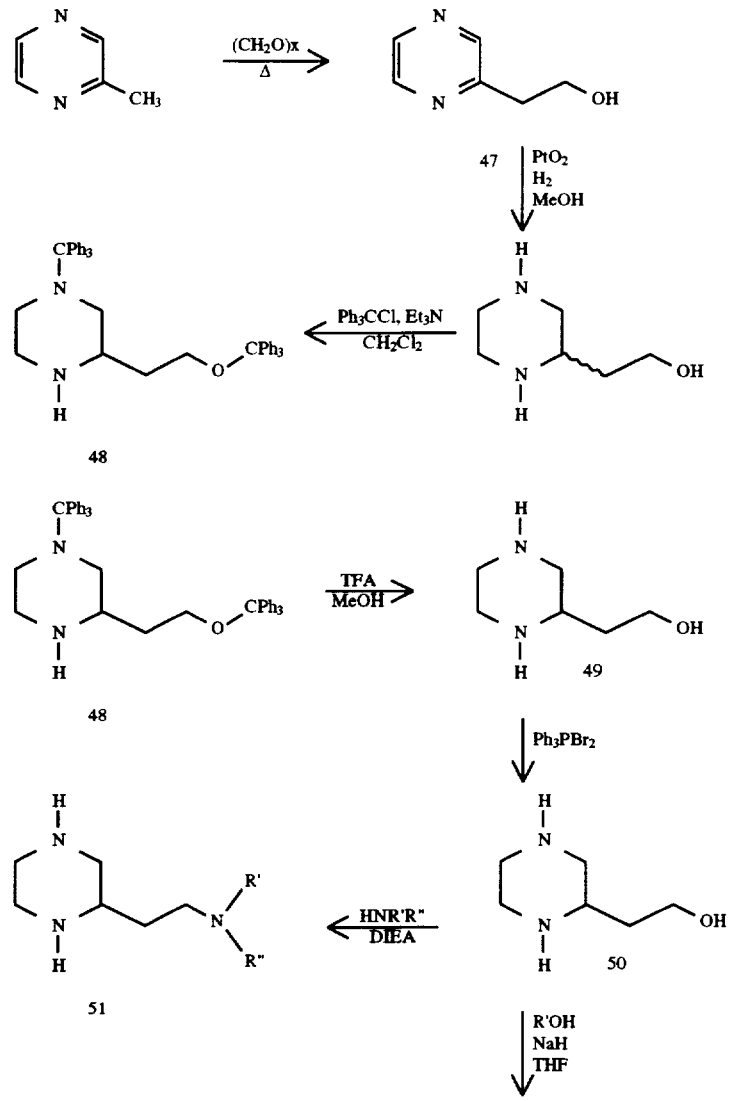

-continued
REACTION SCHEME 16

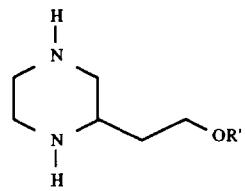

52

Preparation of 2-(2-hydroxyethyl)piperazines and 2-(2-aminoethyl)piperazines can be carried out as illustrated in Scheme 16. Treatment of 2-methylpyrazine with paraformaldehyde at 165° C. (as described by Kitchen and Hanson, *J. Am. Chem. Soc.*, 1951, 73, 1838) provides hydroxyethyl derivatives 47, which may be reduced to 2-(2-hydroxyethyl)piperazine by hydrogenation in the presence of a platinum catalyst. Selective protection with trityl chloride provides the bisprotected compound 48, which may be deprotected to amino alcohol 49, which may be converted to bromide 50 with triphenylphosphine dibromide. Treatment with the appropriate amine or alcohol leads to the corresponding substituted amines 51 or ethers 52 respectively.

The aryl piperazines of Formula I can be further derivatized

The compounds of the present invention are prepared from a variety of substituted natural and unnatural amino acids such as those of formulas 60. The preparation of many of these acids is described in U.S. Pat. No. 5,206,237. The preparation of these intermediates in racemic form is accomplished by classical methods familiar to those skilled in the art (Williams. R. M. *"Synthesis of Optically Active α-Amino Acids"* Pergamon Press: Oxford, 1989; Vol. 7). Several methods exist to resolve (DL)-

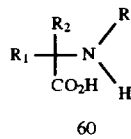

60 amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives (*"Asymmetric Synthesis, Chiral Catalysis"*; Morrison, J. D., Ed; Academic Press: Orlando, Fla., 1985; Vol 5), and (6) enzymatic syntheses (*Angew. Chem. Int. Ed. Engl.* 1978, 17, 176).

For example, alkylation of the enolate of diphenyloxazinone 61 (*J. Am. Chem. Soc.* 1991, 113, 9276) with cinnamyl bromide in the presence of sodium bis(trimethylsilyl)amide proceeds smoothly to afford 62 which is converted into the desired (D)-2-amino-5-phenylpentanoic acid 63 by removing the N-t-butyloxycarbonyl group with trifluoroacetic acid and hydrogenation over a PdCl$_2$ catalyst (Scheme 13).

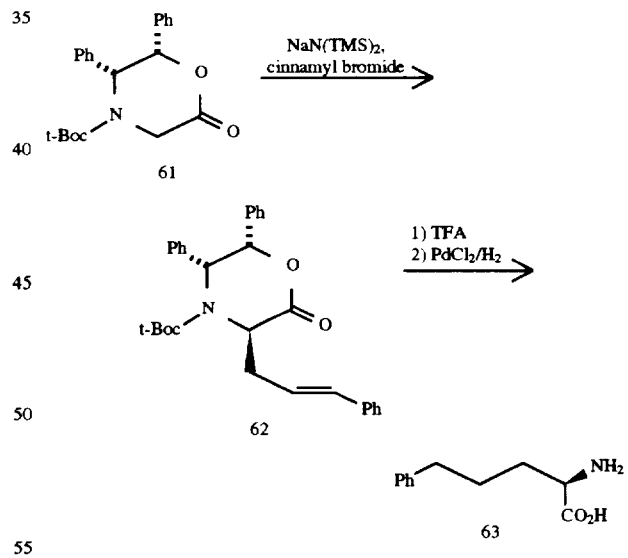

Intermediates of formula 60 which are O-benzyl-(D)-serine derivatives 64 are conveniently prepared from suitably substituted benzyl halides and N-protected-(D)-serine 64. The protecting group L is conveniently a BOC or a CBZ group. Benzylation of 64 can be achieved by a number of methods well known in the literature including deprotonation with two equivalents of sodium hydride in an inert solvent such as DMF followed by treatment with one equivalent of a variety of benzyl halides (*Synthesis* 1989, 36) as shown in Scheme 18.

SCHEME 18

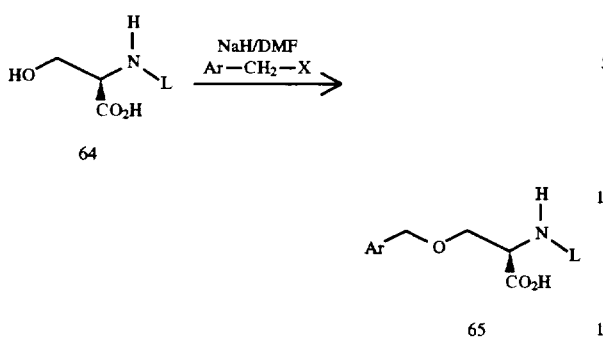

The O-alkyl-(D)-serine derivatives are also prepared using the alkylation protocol shown in Scheme 15. Other methods that could be utilized to prepare (D)-serine derivatives of formula 65 include the acid catalyzed benzylation of carboxyl protected intermediates derived from 64 with reagents of formula $ArCH_2OC(=NH)CCl_{13}$ (O. Yonemnitsu et al., *Chem. Pharm. Bull.* 1988, 36, 4244). Alternatively, alkylation of the chiral gylcine enolates (*J. Am. Chem. Soc.* 1991, 113, 9276; *J. Org. Chem.* 1989, 54, 3916) with $ArCH_2OCH_2X$ where X is a leaving group affords 35. In addition D,L-O-aryl(alkyl)serines may be prepared and resolved by methods described above.

REACTION SCHEME 19

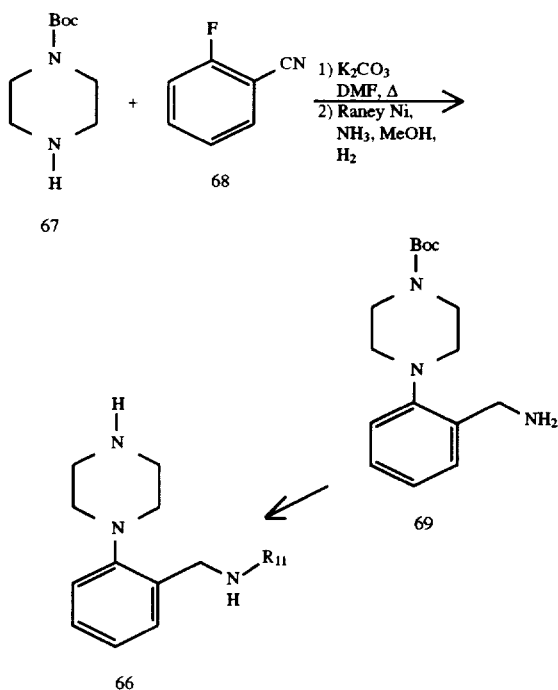

The synthesis of functionalized phenyl-piperazines of formula 66 can be carried out as shown as shown in Scheme 19. Addition of the commercially available piperazine 67 to o-fluoro-benzonitrile 68 proceeds well in the presence of potassium carbonate in DMF. Reduction of nitrile to amine 69 can be carried out by hydrogenation with Raney nickel in methanolic ammonia. The phenyl piperazine intermediate 69 can be derivatized in a variety ways to obtained highly functionalized intermediates of formula 66. Reaction of the amino unit of 69 with sulfonyl chlorides provides sulfonamides, isocyanides yields ureas, acid chlorides or acid anhydrides gives amides, sulfamoyl chlorides gives sulfamides, chloroformates gives carbamates and so on and so forth. Removal of BOC protecting group with acid gives the functionalized intermediate 66 that can be elaborated to the secretagogues used chemistry detailed in Schemes 1–8.

REACTION SCHEME 20

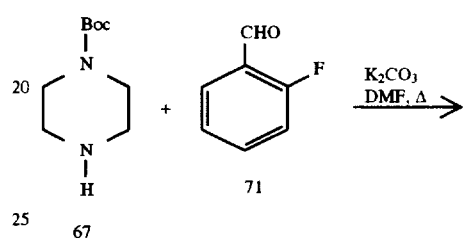

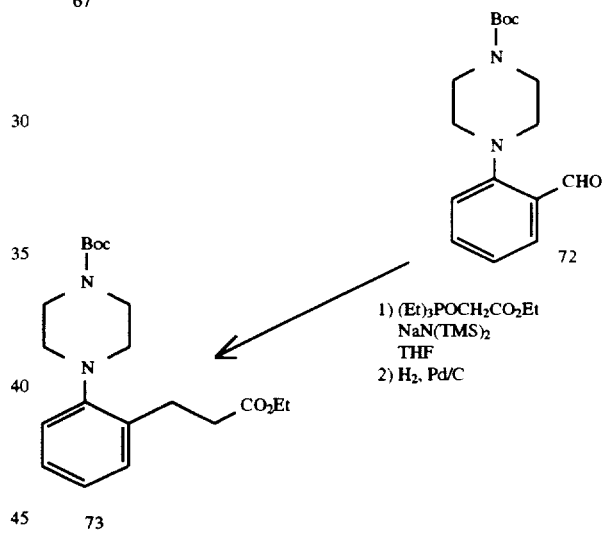

The synthesis of functionalized phenyl-piperazines of formula 70 can be carried out as shown in Scheme 20. Addition of the commercially available piperazine 67 to o-fluoro-benzaldehyde 71 proceeds well in the presence of potassium carbonate in DMF. The phenyl piperazine intermediate 72 can be derivatized in a variety ways to obtained highly functionalized intermediates of formula 70. A Homer-Emmons condensation of 72 with triethylphosphonoacetate and hydrogenation of the a,b-ester intermediate provides 73. Removal of the BOC group of 73 and elaboration to ester bearing GH secretagogues may be carried out by using chemistry detailed in Schemes 1–8.

REACTION SCHEME 21

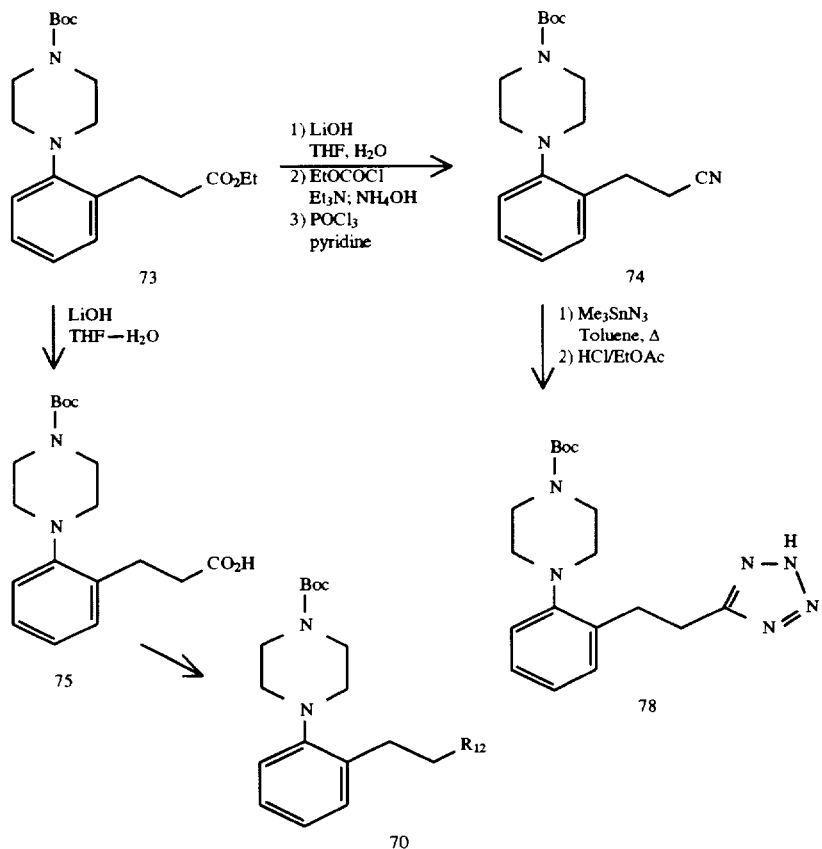

As shown in Scheme 21 the ester unit of 73 can be transformed to the nitrile 74 in a straightforward manner. Reaction of 74 with trimethyltin azide in refluxing toluene provides the tetrazole 78 after removal the BOC protecting group. As shown previously, elaboration of 78 to the tetrazole bearing secretagogues can be carried out by using chemistry detailed in Schemes 1–8 after removal of the protecting group. Other functionalized phenyl piperazines of the formula 70 (wherein $R_{12}$ is a carboxyl derivatized functionality) may be accessed from the intermediate 73 as shown in Scheme 21. The ester unit of 73 can be hydrolyzed with aqueous alkali to give the acid intermediate 75. Peptide type coupling of a variety of amines to 75 provides amides, alcohols gives esters, sulfonamides gives acylsulfonamides (for a procedure see R. T. Jacobs et al. *J. Med Chem.* 1994, 37, 1282–1297). Again removal of the BOC protecting group from these functionalized phenyl piperazines and elaboration to the GH secretagogues is carried by using chemistry presented in Schemes 1–8.

The order of conducting the foregoing reaction schemes may be varied to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention may be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I may also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I may be administered to animals, including man, to release growth hormone in vivo. For example, the compounds may be administered to commercially important animals such as swine, cattle, sheep and the like to accelerate and increase their rate and extent of growth, to improve feed efficiency and to increase milk production in such animals. In addition, these compounds may be administered to humans in vivo as a diagnostic tool to directly determine whether the pituitary is capable of releasing growth hormone. For example, the compounds of Formula I may be administered in vivo to children. Serum samples taken before and after such administration may be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions may comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. No. 4,411,890 and PCT Publications WO 89/07110, WO 89/07111 and B-HT920 as well as hexarelin and the newly discovered GHRP-2 as described in PCT Publication WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HT1D agonists such as sumitriptan or agents which inhibit somatostatin or its release such as physostigmine and pyridostigmine. Preferred growth hormone secretagogues for combination therapy and/or compositions include GHRP-6, GHRP-2, GHRP-1, BHT920, GHRH, IGF-1 and IGF-2.

As is well known to those skilled in the art, the recognized and potential uses of growth hormone are varied and multitudinous. Thus, the administration of the compounds of this invention for purposes of stimulating the release of endogenous growth hormone may have the same effects or uses as growth hormone itself. These varied uses of growth hormone secretagogues may be summarized as follows: stimulating growth hormone release in elderly humans; treating growth hormone deficient adults; prevention of catabolic side effects of glucocorticoids, treatment of osteoporosis, stimulation of the immune system, acceleration of wound healing, accelerating bone fracture repair, treatment of growth retardation, treating acute or chronic renal failure or insufficiency, treatment of physiological short stature, including growth hormone deficient children, treating short stature associated with chronic illness, treatment of obesity and growth retardation associated with obesity, treating growth retardation associated with Prader-Willi syndrome and Turner's syndrome; accelerating the recovery and reducing hospitalization of burn patients or following major surgery such as gastrointestinal surgery; treatment of intrauterine growth retardation, skeletal dysplasia, hypercortisonism and Cushings syndrome; replacement of growth hormone in stressed patients; treatment of osteochondrodysplasias, Noonan's syndrome, sleep disorders, Alzheimer's disease, delayed wound healing, and psychosocial deprivation; treatment of pulmonary dysfunction and ventilator dependency; attenuation of protein catabolic response after a major operation; treating malabsorption syndromes, reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of age-related decline of thymic function; adjunctive therapy for patients on chronic hemodialysis; treatment of immunosuppressed patients and enhancement of antibody response following vaccination; improvement in muscle strength, mobility, maintenance of skin thickness, metabolic homeostasis, renal hemeostasis in the frail elderly; stimulation of osteoblasts, bone remodelling, and cartilage growth; treatment of neurological diseases such as peripheral and drug induced neuropathy, Guillian-Barre Syndrome, amyotrophic lateral sclerosis, multiple sclerosis, cerebrovascular accidents and demyelinating diseases; stimulation of the immune system in companion animals and treatment of disorders of aging in companion animals; growth promotant in livestock; and stimulation of wool growth in sheep.

It will be known to those skilled in the art that there are numerous compounds now being used in an effort to treat the diseases or therapeutic indications enumerated above. Combinations of these therapeutic agents, some of which have also been mentioned above, with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures may be illustrated by combinations of bisphosphonates and the growth hormone secretagogues of this invention. The use of bisphosphonates for these utilities has been reviewed, for example, by Hamdy, N.A.T., Role of Bisphosphonates in Metabolic Bone Diseases. *Trends in Endocrinol. Metab.*, 1993, 4, 19–25. Bisphosphonates with these utilities include alendronate, tiludronate, dimethyl-APD, risedronate, etidronate, YM-175, clodronate, pamidronate, and BM-210995, a preferred bisphosphonate being alendronate. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention may be administered by oral, parenteral (e.g., intramuscular, intraperitoneal, intravenous or subcutaneous injection, or implant), nasal, vaginal, rectal, sublingual, or topical routes of administration and may be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills may additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions may also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They may also be manufactured in the form of sterile solid compositions which may be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the spiriti or scope of the present invention.

INTERMEDIATE 1

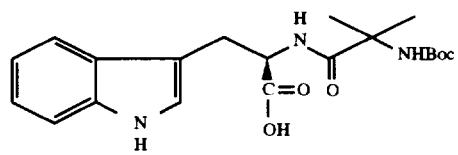

Step A:

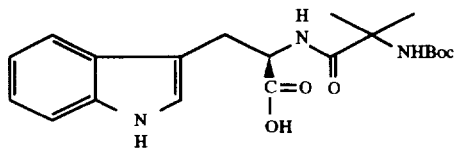

To 5.0 g (16.5 mmole) of the commercially available N-t-BOC-D-tryptophan in 100 mL of chloroform was added 1.80 mL (16.5 mmole) of benzyl alcohol, 0.20 g (1.65 mmole) of 4-N,N-dimethylamino pyridine (DMAP), and 3.20 g of EDC and stirred for 16 h. The reaction mixture was poured into 100 mL of water and the organic layer was separated. The aqueous was further extracted with 2×100 mL of chloroform. The combined organic solution was washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organic solution were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmole) of HOBT, 4.60 g (22.2 mmole) of N-BOC-a-methyl alanine, and 5.32 g (28.0 mmole) of EDC and stirred for 16 h. The reaction mixture was poured into 100 mL of water and the organic layer was separated. The aqueous was further extracted with 2×100 mL of chloroform. The combined organic solution were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO₂; hexane-ethyl acetate as eluent) gave 4.75 g of the desired material as a colorless foam.

¹H NMR (CDCl₃, 200MHz) δ 8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H)

Step B:

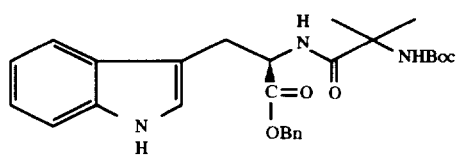

To a solution of 4.75 g of the material from Step A in 100 mL of ethanol was added 1.0 g of 10% Pd/C and stirred at RT under a H₂ balloon for 18 h. The catalyst was filtered off through a pad of celite and washed with ethyl acetate. The filtrate was concentrated to give 2.96 g of the acid as a colorless foam.

¹H NMR (CDCl₃, 200 MHz) δ 8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H).

INTERMEDIATE 2

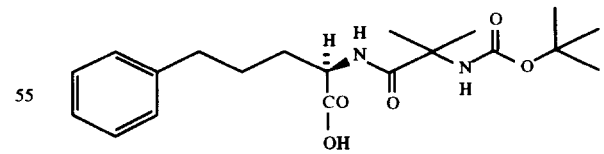

This intermediate was synthesized as described in Step A and B of Intermediate 1, but (2R)-N-t-BOC-5-phenylpentanoic acid (H.

K. Chenault et al. *J. Am. Chem. Soc.* 1989, 111, 6354–6364)) was used in place of N-t-BOC-(D)-tryptophan.

¹H NMR (CDCl₃, 400 MHz) δ 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

37

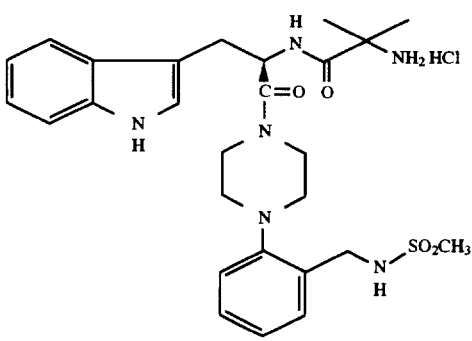

Step A:

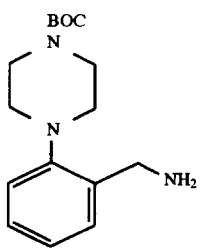

A mixture of 5.0 g of o-fluorobenzonitrile, 9.20 g of N-tBOC-piperazine, and 6.8 g of powdered potassium carbonate was heated at 150° C. in dry DMF for 4 h and cooled to RT and stirred for 2 days. The reaction mixture was poured into 100 mL of water and extracted with 3×50 mL of ethyl acetate. The combined organics were washed with saturated aqueous ammonium chloride solution, 2×50 mL of brine, dried over anhydrous MgSO4 and concentrated. This material was reduced to the benzylamine derivative with Raney Nickel in ethanolic ammonia at 1000 psi at 80° C. for 24h. The catalyst was filtered off through a pad of celite and the filtrate was concentrated.to give the title compound.

$^1$H NMR (400 MHz; CDCl$_3$) δ 8.70 (bs, 2H), 7.42 (d, 1H), 7.34 (t, 1H), 7.20–7.07 (m, 2H), 4.19 (bs, 1H), 3.70–3.40 (m, 4H), 3.90–3.86 (m, 4H), 1.46 (s, 9H)

Step B:

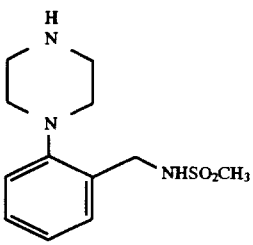

To 0.12 g of the above material in 2 mL of CH$_2$Cl$_2$ at 0° C. was added 0.10 mL of triethylamine and 0.031 mL of methanesulfonyl chloride and stirred for 1 h. The reaction mixture was diluted with 20 mL of CH$_2$Cl$_2$ and washed with 20 mL of saturated NaHCO$_3$, 20 mL of brine, dried over Na$_2$SO$_4$ and concentrated to give an oil which was used in the next step.

Approximately 0.10 g of the above intermediate was treated with CH$_2$Cl$_2$/TFA for 1 h at RT to remove the BOC protecting group. The reaction mixture was evaporated to dryness and basified with saturated NaHCO$_3$ and extracted with CH$_2$Cl$_2$. The combined organics were washed with brine, dried over K$_2$CO$_3$, filtered, and concentrated to give the piperazine intermediate that was used without purification.

38

Step C:

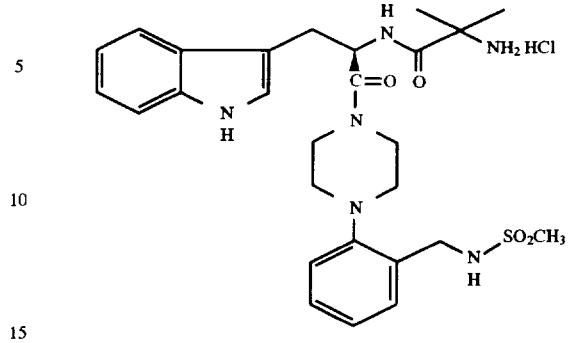

Approximately 40 mg of the piperazine intermediate from Step B was coupled with 69 mg of Intermediate 1 in dry CH$_2$Cl$_2$ in the presence of 10 mg of HOBT and 42 mg of EDC. The reaction mixture was diluted with CH$_2$Cl$_2$ and washed with saturated NaHCO$_3$, brine, dried over Na$_2$SO$_4$, filtered and concentrated. Purification of the crude product on silica gel with hexane-acetone (1:1) as the eluent gave the desired product.

The above intermediate was stirred in a mixture of TFA and CH$_2$Cl$_2$ for 20 min. The reaction mixture was concentrated to dryness, basified with saturated NaHCO$_3$, and extracted with CH$_2$Cl$_2$. The crude product was purified by preparative Tlc on an 1 mm plate with CH$_2$Cl$_2$—MeOH (4:1) as the eluent. This gave a free base that was treated with saturated HCl in EtOAc for 15 min. The reaction was diluted with ether and the precipitate was filtered to give the desired product.

$^1$H NMR (400 MHz, CDCl$_3$) δ 7.62 (d, 1H), 7.41–7.33 (m, 2H), 7.24 (m, 1H), 7.20–7.00 (m, 4H), 6.75 (d, 1H), 5.18 (ddd, 1H), 4.22 (ABq, 2H), 3.90 (bd, 1H), 3.46 (bd, 1H), 3.40–3.25 (m, 2H), 3.22–3.10 (m, 2H), 2.83 (s, 3H), 2.65 (bd, 1H), 2.43 (bd, 1H), 2.07 (bt, 1H), 1.62 (s, 3H), 1.60 (s, 3H), 1.50–1.40 (m, 1H)

EXAMPLE 2

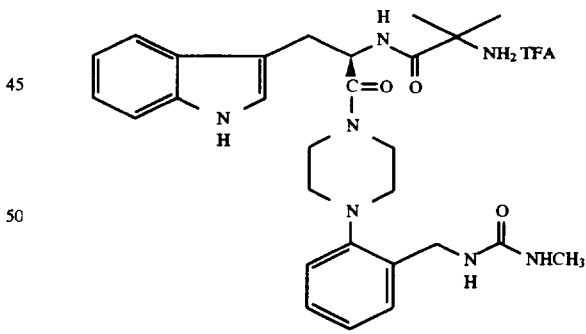

To 0.30 g the benzylamine intermediate prepared in Example 1 Step A in 2 mL of dry CH$_2$Cl$_2$ was added 0.29 mL of triethylamine and 0.10 mL of methylisocyanate and stirred at RT for 40 min. The reaction mixture was concentrated to give a solid.

$^1$H NMR (400 MHz, CDCl$_3$) d 7.30 (d, 1H), 7.22 (t, 1H), 7.10–6.90 (m, 2H), 5.32 (bs, 1H), 5.00 (bs, 1H), 4.66 (bs, 1H), 4.35 (bs, 2H), 3.53 (bs, 4H), 2.80 (bs, 3H), 2.80 (m, 4H), 1.47 (s, 9H)

The above solid was treated with 1 mL of CH$_2$Cl$_2$ and 2 mL of TFA to remove the BOC protecting group, worked-up and elaborated to the title compound as described in Example 1 Steps B & C.

¹H NMR (400 MHz. CD₃OD) δ 8.60 (bs, 1H), 7.70–7.41 (m, 5H), 7.32 (bs, 1H), 7.19 (bt, 1H), 7.10 (bt, 1H), 5.20–5.10 (bs, 1H), 4.26 (bs, 2H), 3.70–3.55 (m, 4H), 3.40–3.31 (m, 6H0, 2.67 (s, 3H), 1.66 (s, 6H)

EXAMPLE 3

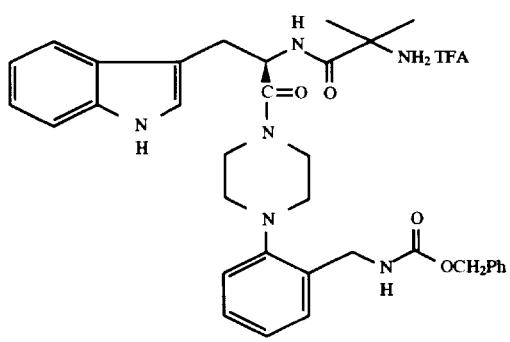

The title compound was prepared by methodology described in Example I Steps A–C, but CBZ-Cl was used in place of methanesulfonyl chloride.

¹H NMR (400 MHz, CD₃OD) δ 7.66 (d, 1H), 7.50–7.00 (m, 12H), 6.83 (d, 1H), 5.30–5.20 9 m, 1H), 5.07 (s, 2H), 3.86 (m, 1H), 3.40 (bd, 1H), 3.30–3.10 (3H), 2.60 (bd, 1H), 2.37 (bd, 1H), 2.06 (bs, 1H), 1.60 (s, 3H), 1.56 (s, 3H), 1.50–1.35 (m, 1H).

EXAMPLE 4

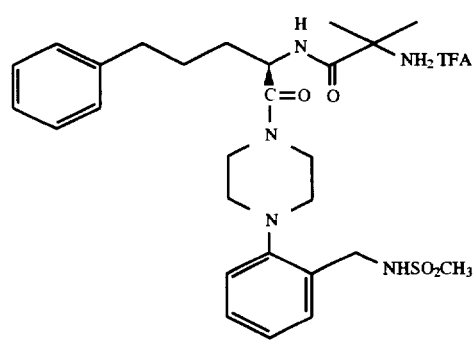

To a stirred solution of 0.15 g of D-N-BOC-3-phenylpropyl glycine in 2 mL of CH₂Cl₂ was added the piperazine methanesulfonamide derivative prepared in Example 1 Step B, 0.082 g of HOBT, 0.147 g of EDC and stirred at RT overnight. The reaction mixture was poured into 30 mL of saturated NaHCO₃ solution, and extracted with 2×30 mL of CH₂Cl₂. The combined organics were washed with 20% aqueous citric acid, 30 mL of brine, dried over MgSO₄, and concentrated.

Approximately 0.10 g of the above coupled product was treated with TFA/CH₂Cl₂ to remove the BOC protecting, the reaction mixture was evaporated to dryness, basified with Na₂CO₃, and extracted with CH₂Cl₂. The combined organics were washed with brine, dried over K₂CO₃, filtered and concentrated.

Approximately 0.070 g of the amine obtained above was coupled with N-BOC-α-methylalanine using the EDC/HOBT procedure described above. Purification of the residue by flash chromatography and removal of the BOC protecting with TFA/CH₂Cl₂ gave the title compound as the trifluoroacetate salt. FAB MS calcd for C27H39N5O4S 529; found 530.8 (m+1)

Alternatively, the HCl salt may be obtained by treatment with dry HCl in EtOAc at ambient temperature for usually 30–60min.

EXAMPLES 5–8

Employing the methodology described in Example 4 the following compounds were prepared either as the free base or TFA or HCl salts.

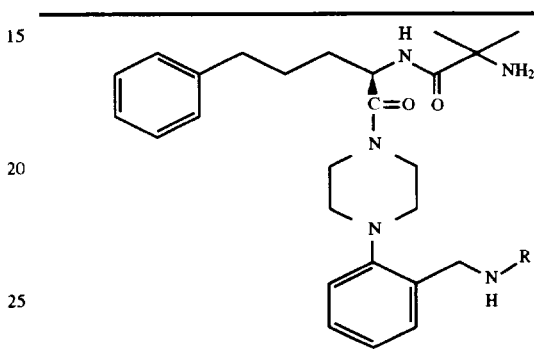

| Example No. | R | molecular formula | FAB MS m/e calc. | m/e found (m + 1) |
|---|---|---|---|---|
| 5 | iPr | C₂₉H₄₃N₅O₄S | 557.30 | 558.60 |
| 6 | CO₂CH₂Ph | C₃₆H₅₁N₅O₆ | 685 | 686.7 |
| 7 | SO₂CH₂CO₂Me | C₂₉H₄₁N₅O₆s | 587.28 | 588.5 |
| 8 | SO₂CH₂COOH | C₂₈H₃₉N₅O₆s | 573.26 | 574.5 |

EXAMPLE 9

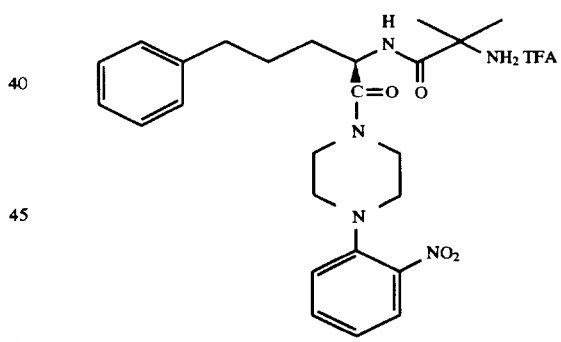

Step A:

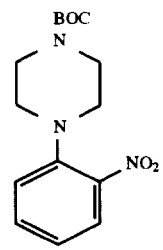

A mixture of 9.8 g of N-tBOC-piperazine, 5.0 g of 1-fluoro-2-nitrobenzene, and 7.3 g of powdered potassium carbonate were heated in 10 mL of dry DMF for 3 h. The solids were filtered off through a pad of celite and washed with ether. The filtrate was washed with saturated aqueous NH₄Cl solution, back extracted with 100 mL of ether. The ether extracts were washed with brine, dried over MgSO₄ and concentrated to give the title compound.

Step B:

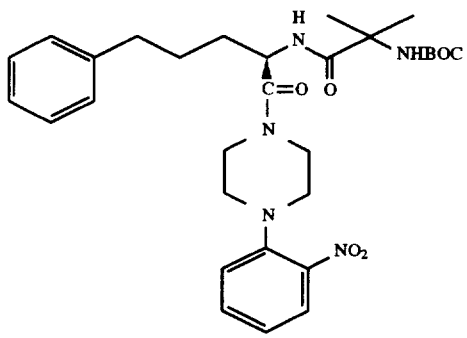

The phenyl piperazine intermediate prepared in Step A was elaborated by using chemistry presented for the preparation of the intermediate obtained in Example 4 Step B.

¹H NMR (400 MHz, CDCl₃) δ 7.79 (d, 1H), 7.50 (t, 1H), 7.28–7.00 (m, 7H), 5.00–4.80 (m, 2H), 3.80–3.52 (m, 3H), 3.50–3.37 (m, 1H), 3.05–2.85 (m, 4H), 3.00–3.86 (m, 2H), 2.80–2.73 (m, 1H), 2.70–2.50 (m, 2H), 1.80–1.60 (m, 5H), 1.48 (s, 3H), 1.46 (s, 3H), 1.40 (s, 9H)

Step C:

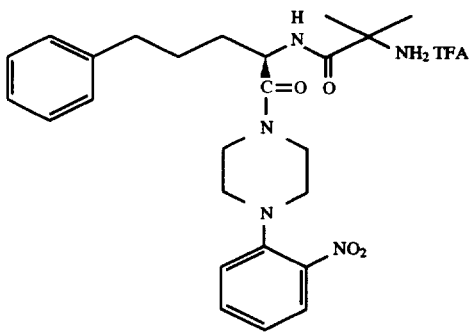

A solution of 12 mg of the intermediate from Step B was treated with 0.50 mL of TFA for 20 min at RT. The volatiles were removed by rotary evaporation and the residue was triturated with ether to give the title compound as a solid.

1H NMR (400 MHz, CD₃OD) δ 7.82 (d, 1H), 7.63 (t, 1H), 7.40–7.10 (m, 7H), 5.00–4.80 (m, 1H), 3.80–3.55 (m, 4H), 3.12–3.00 (m, 3H), 2.96–2.85 (m, 1H), 2.80–2.60 (m, 2H), 2.90–2.70 (m, 4H), 1.61 (s, 6H)

EXAMPLE 10

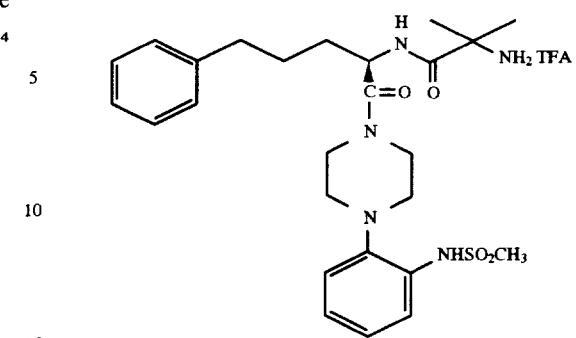

Step A:

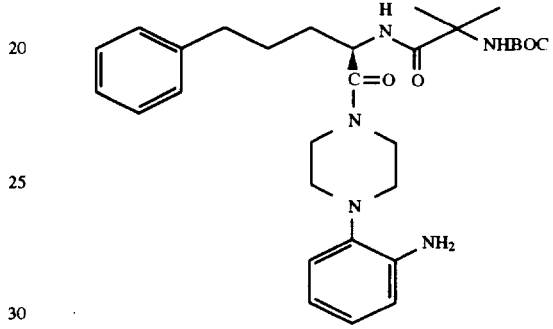

A solution of 2.2 g of the nitro intermediate prepared in Example 9 Step B was reduced to an aniline intermediate by hydrogenation with Raney nickel in 25 mL of ethanol at 40 psi for 3 h. The catalyst was filtered through a pad of celite and washed with ethanol. Concentration of the filtrate gave the desired material.

¹H NMR (400 MHz, CDCl₃) δ 7.27–7.05 (m, 5H), 6.92 (t, 1H), 6.83 (d, 1H), 6.72–6.69 (m, 2H), 4.96 (s, 1H), 4.95–3.86 (m, 1H), 4.20–3.50 (m, 4H), 2.95–2.54 (m, 6H), 1.80–1.52 (m, 2H), 1.60–1.40 (m, 2H), 1.50 (s, 3H), 1.44 (s, 3H), 1.42 (s, 9H)

Step B:

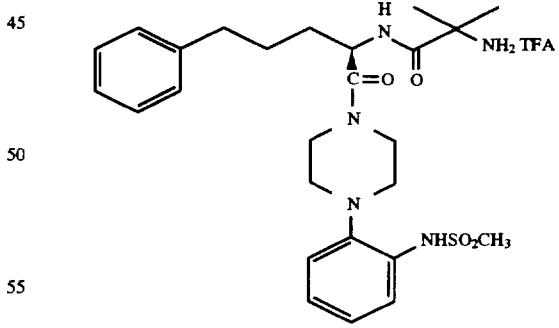

To 0.20 g of the above intermediate in 10 mL of CH₂Cl₂ at 0° C. was added 0.080 mL of N-methylmorpholine, and 0.043 mL of methanesulfonylchloride and stirred for 1 h. Routine work-up and flash chromatography of the residue over silica gel with hexane-ether (5:1) as the eluent gave the desired material. Deprotection with TFA/CH₂Cl₂ gave the title compound.

m/e calcd. for $C_{26}H_{37}N_5O_4S$ 515; found 516.7 (m+1)

Alternatively, the final deprotection may be conducted in HCL/EtOAc to provide the hydrochloride salts of the final products.

EXAMPLES 11–15

The following examples were prepared from the compound of Example 10 Step B.

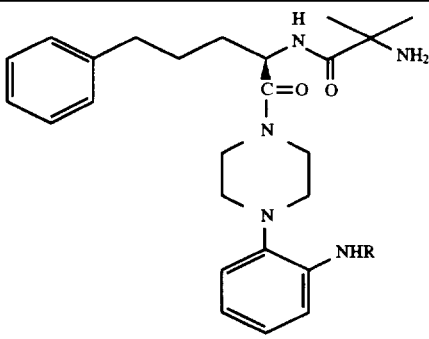

| Example No. | R | molecular formula | FAB MS m/e calc. | m/e found (m + 1) |
|---|---|---|---|---|
| 11 | SO$_2$Ph | $C_{32}H_{41}N_5O_6S$ | 591 | 592.5 |
| 12 | COCH$_2$CH$_2$CO$_2$H | $C_{27}H_{39}N_6O_5$ | 537 | 538 |
| 13 | SO$_2$CH$_2$CO$_2$Me | $C_{28}H_{39}N_5O_6S$ | 573 | 574.8 |
| 14 | SO$_2$CH$_2$COOH | $C_{27}H_{37}N_5O_6S$ | 559 | 560.9 |
| 15 | CO(CH$_3$)$_3$ | $C_{30}H_{43}N_5O_3$ | 521 | 522.9 |

EXAMPLE 16

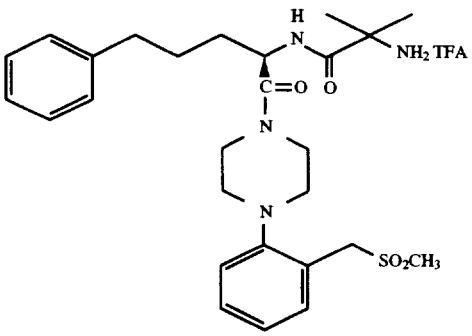

Step A:

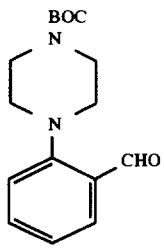

Preparation of this compound was conducted using chemistry described for the preparation of the intermediate synthesized in Example 9 Step A, but o-fluorobenzaldehyde was used in place of o-fluorobenzonitrile.

Step B:

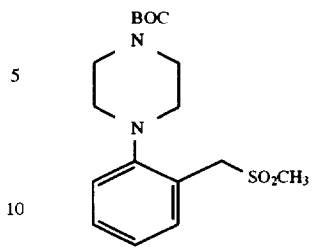

To a solution of 5.0 g of the aldehyde prepared in Step A in 20 mL of dry THF at 0° C. 30 mL of a 2M solution of lithium borohydride in THF and stirred at RT for 2 h. The reaction was quenched with acetone and slowly poured into aqueous NH$_4$Cl solution and extracted with EtOAc. The combined organics were washed with brine, dried over MgSO$_4$ and concentrated.

To a solution of 1.4 g of the alcohol in 10 mL of CH$_2$Cl$_2$ at 0° C. was added 1.3 mL of triethylamine and 0.40 mL of methanesulfonyl chloride and stirred till the reaction was complete as seen by tlc. Routine work-up gave the crude mesylate that was used without purification. To a solution of 1.4 g of the intermediate in 5 mL of dry DMF was added 0.9 g of sodium thiomethoxide and heated at 60° C. overnight.

The reaction mixture was cooled to RT, diluted with brine and extracted with ether. The combined organics were washed with brine, dried over MgSO4 and concentrated. Flash chromatography of the residue with hexane-EtOAc (6:1) as the eluent gave the desired sulfide.

Approximately 0.20 g of the above sulfide was treated with 2 portions of 0.20 g of OXONE in 3 mL of methanol-water (2:1) for 2 h. The reaction mixture poured into brine and extracted with EtOAc (3×20 mL). The combined organics were washed with brine (2×30 mL), died over MgSO$_4$, filtered and concentrated. The residue was purified by silica gel chromatography with hexane-EtOAc (1:1) as the eluent. The BOC protecting group was removed at this time with the TFA/CH$_2$Cl$_2$ procedure and the free base was obtained after NaHCO$_3$ work-up.

Step C:

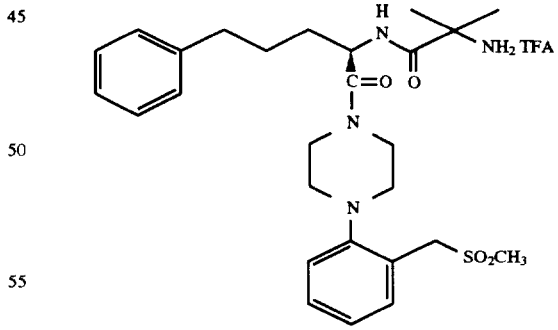

This material was prepared by methodology used to synthesize the intermediate made in Example 1 Step C, but Intermediate 2 was used in place of Intermediate 1. The BOC intermediate thereby obtained was treated with TFA/CH$_2$Cl$_2$ for 30 min at RT and then diluted with ether to give a precipitate that was dried.

$^1$H NMR (400 MHz, CD$_3$OD) δ 7.55 (d, 1H), 7.40 (t, 1H), 7.30–7.10 (m, 7H), 4.60 (s, 2H), 3.80–3.52 (m, 4H), 2.91 (s, 1H), 2.90–2.60 (m, 6H), 1.85–1.70 (m, 4H), 1.61 (s, 6H)

EXAMPLE 17

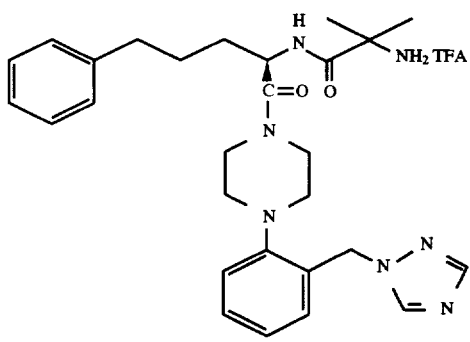

Step A:

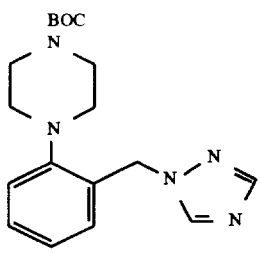

To a solution of 2.23 mmol of the mesylate intermediate prepared as described in Example 17 Step B in 10 mL of dry DMF was added 0.243 g of the sodium salt of 1,2,4-triazole and the resultant solution was stirred overnight. The reaction mixture was diluted with 15 mL of EtOAc and washed with saturated NH$_4$Cl (10 mL), brine (10 mL), dried over MgSO$_4$ and concentrated to the triazole as a yellow solid.

1H NMR (400 MHz, CDCl$_3$) δ 8.05 (s, 1H), 7.86 (s, 1H), 7.36–7.05 (m, 4H), 5.40 (s, 2H), 3.48 (bs, 4H), 2.73 (bs, 4H), 1.43 (s, 9H) (this NMR also showed traces of DMF and 1,2,4-triazole).

Step B:

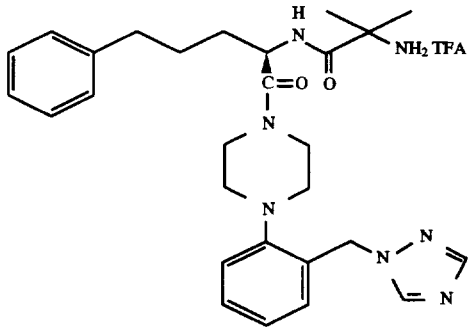

The above intermediate was deprotected, coupled with Intermediate 2, and finally deprotected by employing methodology described for the preparation of the intermediates in Example 1.

EXAMPLES 18–22

The following compounds were prepared employing methodology used to synthesize the title compound of Example 4 with the following modifications: a) N-BOC-D-tryptophan was used in place of D-3-phenylpropylglycine, b) either methanol/concentrated HCl or TFA/CH$_2$Cl$_2$ were used to remove the BOC protecting group. The characteristic NMR resonances reported are either for the salt form (in CD$_3$OD) or the free base obtained after basic work-up (in CDCl$_3$).

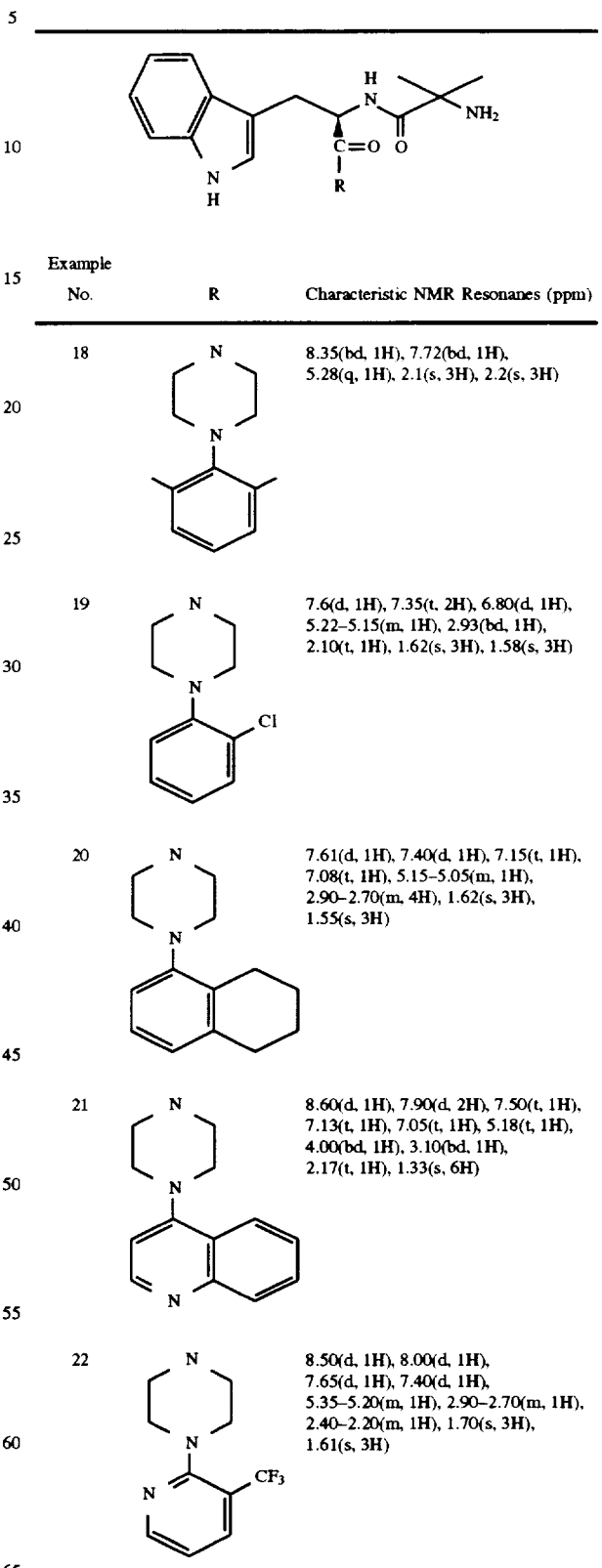

EXAMPLE 23

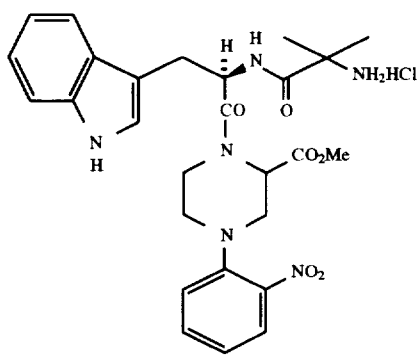

Step A:

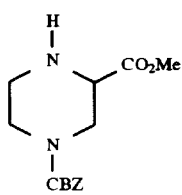

A mixture of 500 mg of piperazine-4-CBZ-2-carboxylic acid (*J. BioMed. Chem. Lett.* 1993, 3, 2023), and 164 ml of thionyl chloride was refluxed in methanol for 12 hours and cooled to RT. The resulting mixture was concentrated. The residue in chloroform was washed with 1 N NaOH, brine, dried over anhydrous potassium carbonate and concentrated to give the title compound (419 mg).

Step B:

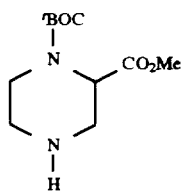

To a solution of the above material (337 mg) in chloroform was added di-t-butyl dicarbonate at RT. After stirring for 3 hours, the mixture was concentrated. The residue in methanol was hydrogenated over a catalytic amount of Pd(OH)$_2$ at one atmosphere. The mixture was stirred for 12 hours and then filtered though Celite. The filtrate was concentrated to give the title compound (295 mg).

Step C:

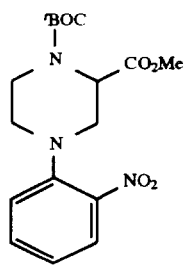

A mixture of the above material (250 mg), o-fluoronitrobenzene (129 ml) and potassium carbonate (168 mg) was heated at 100 C. in DMF for 12 hours. The mixture was poured into water and extracted with ether (3X). The organic layers were washed with water (5X), brine, dried over sodium sulfate and concentrated. The residue was purified by PLC (hexanes/ethyl acetate=5/1) to give the title compound (250 mg ).

$^1$H NMR (CDCl$_3$, 400 MHz): δ 7.66 (d, 8 Hz, 1 H), 7.47 (t, 8 Hz, 1H), 7.17 (d, 8 Hz, 1 H), 7.12 (t, 8 Hz, 1 H), 4.81 (s, 1/2 H), 4.62 (s, 1/2 H), 3.95–3.35 (m, 4 H), 3.77 (s, 3/2 H), 3.75 (s, 3/2 H), 3.17–3.07 (m, 2 H), 2.86 (m, 1 H), 1.47 (s, 9/2 H), 1.43 (s, 9/2 H).

Step D:

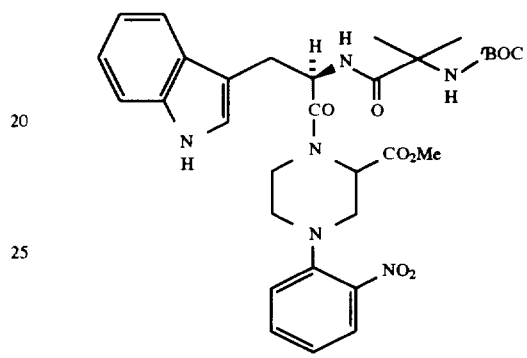

To the intermediate prepared in Step C (250 mg) was added 2 ml of TFA. After 10 minutes, the mixture was concentrated. The residue was dissolved in chloroform and washed with 1N NaOH, brine and dried over potassium carbonate. The organic layer was concentrated. The residue in 5 ml of chloroform was coupled with Intermediate 1 (255 mg) in the presence of BOP reagent (450 mg). After stirring for 12 hours, the mixture was poured into water and extracted with methylene chloride, dried over sodium sulfate and concentrated. The residue was purified by chromatatron (hexanes/ethyl acetate=1/1) to give the desired product (140 mg).

Step E:

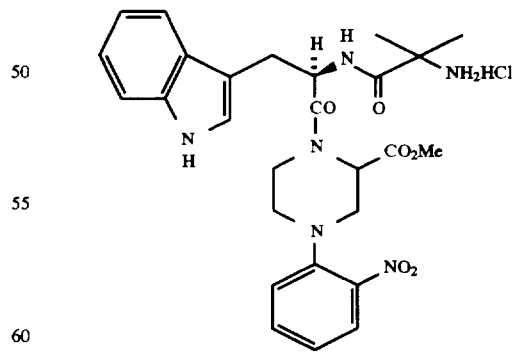

Through a solution of the above intermediate (5 mg) in ethyl acetate was bubbled HCl(g) at 0° C. for 15 seconds. After standing for 30 minutes, the mixture was concentrated to give the title compound (4.3 mg). FAB-MS: 537.5 (M+1).

EXAMPLE 24

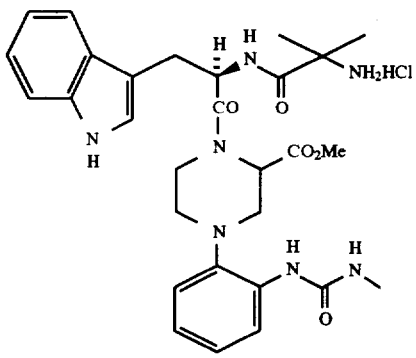

Step A:

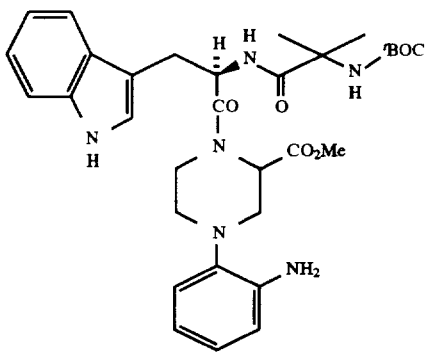

The intermediate obtained from Example 23, Step D (130 mg) was reduced to the aniline derivative with Raney Nickel in methanol at 50 psi for 12 hours. The catalyst was filtered off though Celite and the filtrate was concentrated to give the title compound (65 mg).

Step B:

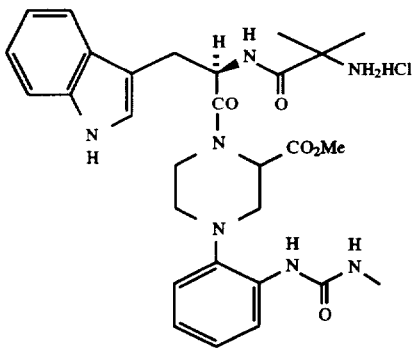

To the intermediate obtained form Step A (13 mg), in chloroform was added methyl isocyanate (4 ml) and refluxed for 3 hours. The mixture was concentrated and purified by chromatatron (methylene chloride/methanol=20/1) to give desire product. The above intermediate in ethyl acetate was bubbled though HCl(g) at 0° C. for 15 seconds. After standing for 30 minutes, the mixture was concentrated to give the title compound (8.9 mg). FAB-MS: 564.3 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

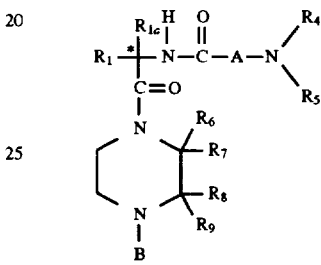

wherein:

$R_1$ is selected from the group consisting of: $C_1-C_{10}$ alkyl-, aryl-, aryl($C_1-C_6$ alkyl)-, heteroaryl-, heteroaryl($C_1-C_6$ alkyl)-, ($C_3-C_7$ cycloalkyl)-($C_1-C_6$ alkyl)-, ($C_1-C_5$ alkyl)-K—($C_1-C_5$ alkyl)-, aryl-($C_0-C_5$ alkyl)-K—($C_1-C_5$ alkyl)-, heteroaryl-($C_0-C_5$ alkyl)-K—($C_1-C_5$ alkyl)-, and ($C_3-C_7$ cycloalkyl)-($C_0-C_5$ alkyl)-K—($C_1-C_5$ alkyl)-, wherein K is —O—, —S(O)$_m$—, —N($R_2$)C(O)—, —C(O)N($R_2$)—, —OC(O)—, —C(O)O—, —CR$_2$=CR$_2$— or —C≡C—.

wherein $R_2$ and the alkyl groups may be further substituted with 1 to 9 halo, —S(O)$_m$R$_{2a}$, 1 to 3 of —OR$_{2a}$, or —C(O)OR$_{2a}$, and wherein aryl is phenyl or naphthyl, and heteroaryl is selected from indolyl, thiophenyl, furanyl, benzothipheneyl, benzofuranyl, pyridinyl, quinolinyl, triazolyl, imidazolyl, thiazolyl, and benzimidazolyl, wherein aryl and heteroaryl are unsubstituted or substituted with phenyl, phenoxy, halophenyl, 1 to 3 of —C$_1$-C$_6$ alkyl, 1 to 3 of halo, 1 to 2 of —OR$_2$, methylenedioxy, —S(O)$_m$R$_2$, 1 to 2 of —CF$_3$, —OCF$_3$, nitro, —N(R$_2$)(R$_2$), —N(R$_2$)C(O)(R$_2$), —C(O)OR$_2$, —C(O)N(R$_2$)(R$_2$), —SO$_2$N(R$_2$)(R$_2$), —N(R$_2$)SO$_2$-aryl, or —N(R$_2$)SO$_2$R$_2$;

$R_{1a}$ is hydrogen or $C_1-C_4$ alkyl;

$R_2$ is selected from the group consisting of: hydrogen, —$C_1-C_6$ alkyl, —$C_3-C_7$ cycloalkyl, and —CH$_2$-phenyl, wherein the alkyl or the cycloalkyl is unsubstituted or substituted with hydroxyl, $C_1-C_3$ alkoxy, thioalkyl, C(O)OR$_{2a}$, and wherein, if two —$C_1-C_6$ alkyl groups are present on one atom, the groups may be optionally joined to form a $C_3-C_8$ cyclic ring optionally including oxygen, sulfur, or —NR$_{2a}$, the $C_3-C_8$ cyclic ring being selected from the group consisting of pyrrolidine, piperidine, piperazine, morpholine, thiomorpholine;

$R_{2a}$ is hydrogen or $C_1-C_6$ alkyl;

51

R$_4$ and R$_5$ are independently selected from the group consisting of: hydrogen, C$_1$-C$_6$ alkyl, substituted C$_1$-C$_6$ alkyl wherein the substituents may be 1 to 5 halo, 1 to 3 hydroxy, 1 to 3 C$_1$-C$_{10}$ alkanoyloxy, 1 to 3 C$_1$-C$_6$ alkoxy, phenyl, phenoxy, 2-furyl, C$_1$-C$_6$ alkoxycarbonyl, —S(O)$_m$(C$_1$-C$_6$ alkyl); or wherein R$_4$ and R$_5$ may be taken together to form —(CH$_2$)$_r$L$_a$(CH$_2$)$_s$—, wherein L$_a$ is —C(R$_2$)$_2$—, —O—, —S(O)$_m$—or —N(R$_2$)—, wherein r and s are independently 1 to 3, and R$_2$ is as defined above;

R$_6$ and R$_8$ are independently selected from the group consisting of: hydrogen, —C$_1$-C$_{10}$ alkyl, —(CH$_2$)$_q$-aryl, —(CH$_2$)$_q$C(O)OR$_2$, —(CH$_2$)$_q$C(O)N(R$_2$)(R$_2$), —(CH$_2$)$_q$(C$_3$-C$_6$ cycloalkyl), —(CH$_2$)$_q$—K—(C$_1$-C$_6$ alkyl), —(CH$_2$)$_q$—K—(CH$_2$)$_r$-aryl, —(CH$_2$)$_q$—K—(CH$_2$)$_r$—(C$_3$-C$_7$ cycloalkyl), wherein K is —O—, —S(O)$_m$—, —CH=CH—, —C≡C—, —N(R$_2$)C(O)—, —C(O)NR$_2$—, —C(O)O—, or —OC(O)—, wherein the alkyl, —R$_2$, —(CH$_2$)$_q$— and —(CH$_2$)$_r$— groups may be optionally substituted by —C$_1$-C$_4$ alkyl, hydroxyl, —C$_1$-C$_4$ alkoxy, carboxyl or carboxylate-C$_1$-C$_4$ esters, and wherein aryl is phenyl, unsubstituted or substituted with 1 to 3 halo, 1 to 3 —OR$_2$, —C(O)OR$_2$, 1 to 3 —C$_1$-C$_4$ alkyl, —S(O)$_m$R$_2$, or 1H-tetrazol-5-yl;

R$_7$ and R$_9$ are independently selected from the group consisting of: hydrogen, —C$_1$-C$_{10}$ alkyl, —(CH$_2$)$_r$-aryl, wherein aryl is phenyl, unsubstituted or substituted with 1 to 3 halo, 1 to 3 —OR$_2$, —C(O)OR$_2$, 1 to 3 —C$_1$-C$_4$ alkyl, —S(O)$_m$R$_2$, or 1H-tetrazolyl;

A is:

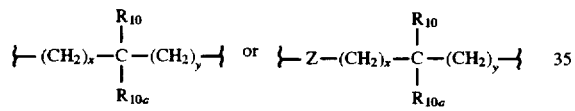

wherein x and y are independently 0, 1, 2 or 3; Z is —N(R$_9$)— or —O—, wherein R$_9$ is hydrogen or C$_1$-C$_6$ alkyl; R$_{10}$ and R$_{10a}$ are independently selected from the group consisting of: hydrogen, —C$_1$-C$_6$ alkyl, trifluoromethyl, phenyl, and substituted C$_1$-C$_6$ alkyl wherein the substituents are selected from the group consisting of: imidazolyl, phenyl, indolyl, p-hydroxyphenyl, —OR$_2$, —S(O)$_m$R$_2$, —C(O)OR$_2$, —C$_3$-C$_7$ cycloalkyl, —N(R$_2$)(R$_2$), and —C(O)N(R$_2$)(R$_2$);

or R$_{10}$ and R$_{10a}$ may independently be joined to one or both of R$_4$ and R$_5$ groups to form alkylene bridges between the terminal nitrogen and the alkyl portion of the R$_{10}$ or R$_{10a}$ groups, wherein the bridge contains 1 to 5 carbons atoms;

B is selected from the group consisting of: phenyl, naphthyl, indolyl, thiophenyl, furanyl, benzothiopheneyl, benzofuranyl, pyridinyl, quinolinyl, triazolyl, imidazolyl, thiazolyl, and benzimidazolyl, which is unsubstituted or substituted with one or more substituents selected from the group consisting of: hydrogen, —C$_1$-C$_6$ alkyl, —(CH$_2$)$_r$—(C$_5$-C$_6$ cycloalkyl), —(CH$_2$)$_r$-aryl, —O—R$_2$, —O—(CH$_2$)$_r$-aryl, —C(O)(CH$_2$)$_r$-aryl, cyano, nitro, halo, —(CH$_2$)$_q$OR$_2$, —(CH$_2$)$_q$CH(OR$_2$)R$_2$, —(CH$_2$)$_q$CH(OR$_2$)—(CH$_2$)$_r$-aryl, —(CH$_2$)$_q$C(O)OR$_2$, —(CH$_2$)$_q$C(O)O(CH$_2$)$_r$-aryl, —(CH$_2$)$_q$C(O)O(CH$_2$)$_r$—(C$_5$-C$_6$ cycloalkyl), —(CH$_2$)$_q$C(O)N(R$_2$)(R$_2$), —(CH$_2$)$_q$C(O)N(R$_2$)(CH$_2$)$_r$-aryl, —(CH$_2$)$_q$C(O)N(R$_2$)(CH$_2$)$_r$—

52

(C$_5$-C$_6$ cycloalkyl), —(CH$_2$)$_q$N(R$_2$)C(O)(R$_2$), —(CH$_2$)$_q$N(R$_2$)C(O)(CH$_2$)$_r$-aryl, —(CH$_2$)$_q$N(R$_2$)C(O)N(R$_2$)(R$_2$), —(CH$_2$)$_q$N(R$_2$)C(O)N(R$_2$)(CH$_2$)$_r$-aryl, —(CH$_2$)$_q$N(R$_2$)C(O)OR$_2$, —(CH$_2$)$_q$N(R$_2$)C(O)O(CH$_2$)$_r$-aryl, —(CH$_2$)$_q$N(R$_2$)SO$_2$R$_2$, —(CH$_2$)$_q$N(R$_2$)SO$_2$(CH$_2$)$_r$-aryl, —(CH$_2$)$_q$SO$_2$R$_2$, —(CH$_2$)$_q$SO$_2$(CH$_2$)$_r$- aryl, —(CH$_2$)$_q$SO$_2$N(R$_2$)(R$_2$), —(CH$_2$)$_q$SO$_2$N(R$_2$)(CH$_2$)$_r$-aryl, —(CH$_2$)$_q$SO$_2$N(R$_2$)C(O)R$_2$, —(CH$_2$)$_q$SO$_2$N(R$_2$)C(O)-aryl, —(CH$_2$)$_q$C(O)NHSO$_2$R$_2$, —(CH$_2$)$_q$(1H-tetrazol-5-yl), —(CH$_2$)$_q$(imidazol-2-yl), —(CH$_2$)$_q$(1,2,4-triazol-1-yl), —(CH$_2$)$_q$CONH(1H-tetrazol-5-yl), —(CH$_2$)$_q$CONH(imidazol-2-yl), and —(CH$_2$)$_q$CONH(1,2,4-triazol-1-yl), wherein aryl is phenyl unsubstituted or substituted with 1 to 2 halo, amino, 1 to 2 —OR$_2$, or 1 to 2 —(C$_1$-C$_4$ alkyl);

m is 0, 1, or 2;

n is 1 or 2;

q is 0, 1, 2, 3 or 4;

t is 0, 1, 2 or 3;

and pharmaceutically acceptable salts and individual diastereomers thereof.

2. The compound of claim 1 wherein:

R$_1$ is selected from the group consisting of: C$_1$-C$_{10}$ alkyl, aryl(C$_1$-C$_4$ alkyl)-, C$_5$-C$_6$ cycloalkyl-(C$_1$-C$_4$ alkyl)-, (C$_1$-C$_4$ alkyl)-K—C$_1$-C$_2$ alkyl-, aryl(C$_0$-C$_2$ alkyl)-K—(C$_1$-C$_2$ alkyl)-, C$_3$-C$_6$cycloalkyl(C$_0$-C$_2$alkyl)-K—(C$_1$-C$_2$alkyl)-, wherein K is O or S(O)$_m$, and the aryl is phenyl, unsubstituted or substituted by 1 to 2 —C$_1$-C$_4$ alkyl, 1 to 2 halo, —OR$_2$, —C(O)OR$_2$, —CF$_3$ or —S(O)$_m$R$_2$;

R$_2$ is selected from the group consisting of: hydrogen, C$_1$-C$_6$ alkyl, C$_3$-C$_6$ cycloalkyl, wherein the alkyl or the cycloalkyl is unsubstituted or substituted with hydroxyl, C$_1$-C$_3$ alkoxy, thioalkyl, C(O)OR$_{2a}$, and, if two C$_1$-C$_6$ alkyls are present on one atom, they may be optionally joined to form a C$_5$-C$_6$ cyclic ring optionally including the heteroatoms oxygen or NR$_{2a}$, the C$_3$-C$_8$ cyclic ring being selected from the group consisting of pyrrolidine, piperidine, piperazine, morpholine, thiomorpholine;

R$_{2a}$ is hydrogen or C$_1$-C$_4$ alkyl;

R$_4$ and R$_5$ are independently selected from the group consisting of: hydrogen, C$_1$-C$_4$ alkyl, substituted C$_1$-C$_4$ alkyl wherein the substituents may be 1 to 2 hydroxy or S(O)$_m$(C$_1$-C$_3$alkyl);

R$_6$ and R$_8$ are independently selected from the group consisting of: hydrogen, —C$_1$-C$_{10}$ alkyl, —(CH$_2$)$_r$-aryl, —(CH$_2$)$_q$C(O)OR$_2$, —(CH$_2$)$_q$C(O)N(R$_2$)(R$_2$), —(CH$_2$)$_q$(C$_3$-C$_6$ cycloalkyl), —(CH$_2$)$_n$—K—(C$_1$-C$_6$ alkyl), —(CH$_2$)$_n$—K—(CH$_2$)$_r$-aryl, —(CH$_2$)$_n$—K—(CH$_2$)$_r$—(C$_3$-C$_7$ cycloalkyl), wherein K is —O—, —S(O)$_m$—, —N(R$_2$)C(O)—, —C(O)NR$_2$—, —C(O)O—, or —OC(O)—, wherein the alkyl, —R$_2$, —(CH$_2$)$_q$— and —(CH$_2$)$_r$— groups may be optionally substituted by —C$_1$-C$_4$ alkyl, hydroxyl, —C$_1$-C$_4$ alkoxy, carboxyl or carboxylate-C$_1$-C$_4$ esters, and wherein aryl is phenyl, unsubstituted or substituted with 1 to 3 halo, 1 to 3 —OR$_2$, —C(O)OR$_2$, 1 to 3 —C$_1$-C$_4$ alkyl, —S(O)$_m$R$_2$, or 1 H-tetrazolyl;

R$_7$ and R$_9$ are independently selected from the group consisting of: hydrogen, —C$_1$-C$_{10}$ alkyl, —(CH$_2$)$_r$-aryl, wherein the aryl group may be optionally substituted with 1 to 3 halo, 1 to 3 —OR$_2$, —C(O)OR$_2$, 1 to 3 —C$_1$-C$_4$ alkyl, —S(O)$_m$R$_2$ or 1H-tetrazol-5-yl;

A is:

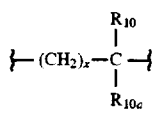

wherein x is 0 or 1;

$R_{10}$ and $R_{10a}$ are independently selected from the group consisting of: hydrogen, and $C_1$–$C_3$ alkyl; or $R_{10}$ and $R_{10a}$ can independently be joined to one or both of the $R_4$ and $R_5$ groups to form alkylene bridges between the terminal nitrogen and the alkyl portion of the $R_{10}$ or $R_{10a}$ groups to form 5 or 6 membered rings containing the terminal nitrogen;

B is selected from the group consisting of: phenyl, indolyl, pyridinyl, and pyrimidinyl, unsubstituted or substituted with one or more substituents selected from the group consisting of: hydrogen, —$C_1$–$C_6$ alkyl, —$(CH_2)_t$,—$(C_5$–$C_6$ cycloalkyl), —$(CH_2)_t$-aryl, —O—$R_2$, —O—$(CH_2)_t$-aryl, —C(O)$(CH_2)_t$-aryl, cyano, nitro, halo, —$(CH_2)_qOR_2$, —$(CH_2)_qCH(OR_2)$ $R_2$, —$(CH_2)_qCH(OR_2)$—$(CH_2)_t$-aryl, —$(CH_2)_qC(O)$ $OR_2$, —$(CH_2)_qC(O)O(CH_2)_t$-aryl, —$(CH_2)_qC(O)O$ $(CH_2)_t$-$(C_5$–$C_6$ cycloalkyl), —$(CH_2)_qC(O)N(R_2)(R_2)$, —$(CH_2)_qC(O)N(R_2)(CH_2)_t$-aryl, —$(CH_2)_qC(O)N(R_2)$ $(CH_2)_t$-$(C_5$–$C_6$ cycloalkyl), —$(CH_2)_qN(R_2)C(O)(R_2)$, —$(CH_2)_qN(R_2)C(O)(CH_2)_t$-aryl, —$(CH_2)_qN(R_2)C(O)$ $N(R_2)(R_2)$, —$(CH_2)_qN(R_2)C(O)N(R_2)(CH_2)_t$-aryl, —$(CH_2)_qN(R_2)C(O)OR_2$, —$(CH_2)_qN(R_2)C(O)O$ $(CH_2)_t$-aryl, —$(CH_2)_qN(R_2)C(O)N(R_2)(R_2)$, —$(CH_2)_q$ $N(R_2)C(O)N(R_2)(CH_2)_t$-aryl, —$(CH_2)_qN(R_2)C(O)$ $OR_2$, —$(CH_2)_qN(R_2)C(O)O(CH_2)_t$-aryl, —$(CH_2)_qN$ $(R_2)SO_2R_2$, —$(CH_2)_qN(R_2)SO_2(CH_2)_t$-aryl, —$(CH_2)_q$ $SO_2R_2$, —$(CH_2)_qSO_2(CH_2)_t$-aryl, —$(CH_2)_qSO_2N(R_2)$ $(R_2)$, —$(CH_2)_qSO_2N(R_2)(CH_2)_t$-aryl, —$(CH_2)_qSO_2N$ $(R_2)C(O)R_2$, —$(CH_2)_qSO_2N(R_2)C(O)$-aryl, —$(CH_2)_q$ $C(O)NHSO_2R_2$, —$(CH_2)_q(1H$-tetrazol-5-yl), —$(CH_2)_q$ (imidazol-2-yl), —$(CH_2)_q(1,2,4$-triazol-1-yl), —$(CH_2)_q$ CONH(1H-tetrazol-5-yl), —$(CH_2)_q$CONH (imidazol-2-yl), and —$(CH_2)_q$CONH(1,2,4-triazol-1-yl), wherein aryl is phenyl, unsubstituted or substituted with 1 to 2 halo, amino, 1 to 2 —$OR_2$, or 1 to 2 —($C_1$–$C_4$ alkyl), m is 0, 1 or 2;

n is 1 or 2;

q is 0, 1, 2 or 3;

t is 0, 1, 2 or 3;

and pharmaceutically acceptable salts and individual diastereomers thereof.

3. A compound of the formula:

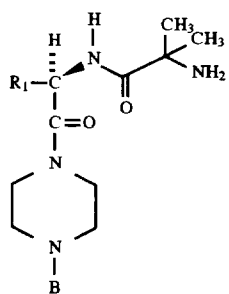

wherein $R_1$ is selected from the group consisting of:

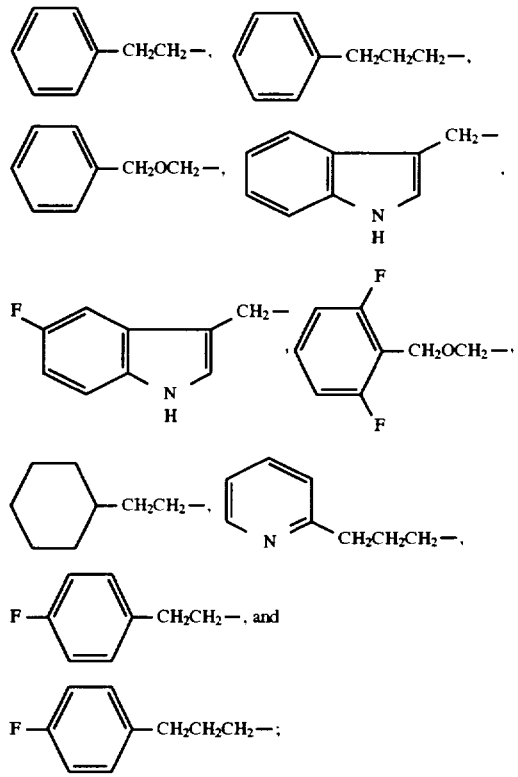

B is phenyl unsubstituted or substituted with one or more substituents selected from the group consisting of: hydrogen, —$(CH_2)_t$-aryl, $C_1$–$C_3$ alkyl, —$(CH_2)_qOR_2$, —$(CH_2)_qC(O)OR_2$, —$(CH_2)_qC(O)O(CH_2)_t$-aryl, —$(CH_2)_q$ $C(O)N(R_2)(R_2)$, —$(CH_2)_qC(O)N(R_2)(R_2)$, —$(CH_2)_qC(O)N$ $(R_2)(CH_2)_t$-aryl, —$(CH_2)_qN(R_2)C(O)(R_2)$, —$(CH_2)_qN(R_2)$ $C(O)N(R_2)(R_2)$, —$(CH_2)_qN(R_2)C(O)OR_2$, —$(CH_2)_qN(R_2)$ $SO_2R_2$, —$(CH_2)_qN(R_2)SO_2(CH_2)_t$-aryl, —$(CH_2)_q$ $SO_2R_2$, —$(CH_2)_qSO_2(CH_2)_t$-aryl, —$(CH_2)_qSO_2N(R_2)(R_2)$, —$(CH_2)_qSO_2N(R_2)(CH_2)_t$-aryl, —$(CH_2)_qSO_2N(R_2)C(O)$ $R_2$, —$(CH_2)_qSO_2N(R_2)C(O)$-aryl, —$(CH_2)_qC(O)$ $NHSO_2R_2$, —$(CH_2)_q(1H$-tetrazol-5-yl), —$(CH_2)_q$ (imidazol-2-yl), —$(CH_2)_q(1,2,4$-triazol-1-yl), —$(CH_2)_q$ CONH(1H-tetrazol-5-yl), —$(CH_2)_q$CONH(imidazol-2-yl), and —$(CH_2)_q$CONH(1,2,4-triazol-1-yl), wherein aryl is phenyl unsubstituted or substituted with 1 to 2 halo, amino, 1 to 2 —$OR_2$, or 1 to 2 —($C_1$–$C_4$ alkyl);

$R_2$ is selected from the group consisting of: hydrogen, —$C_1$–$C_6$ alkyl, —$C_3$–$C_7$ cycloalkyl, and —CH2-phenyl, optionally substituted with hydroxyl, $C_1$–$C_3$-alkoxy, thiomethyl, —C(O)$OR_{2a}$, wherein if two —$C_1$–$C_6$ alkyl groups are present on one atom, the groups may be optionally joined to form a $C_3$–$C_4$ cyclic ring optionally including oxygen, sulfur or —$NR_{2a}$;

$R_{2a}$ is hydrogen or $C_1$–$C_6$ alkyl;

q is 0, 1, 2 or 3;

t is 0, 1, or 2;

and the pharmaceutically acceptable salts and individual diastereomers thereof.

4. The stereospecific compound of claim 1 which is:
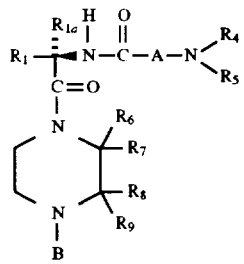
wherein $R_1$, $R_{1a}$, $R_4$, $R_5$, $R_6$, $R_7$, $R_8$, $R_9$, A and B are are as defined in claim 1.
5. A compound which is selected from the group
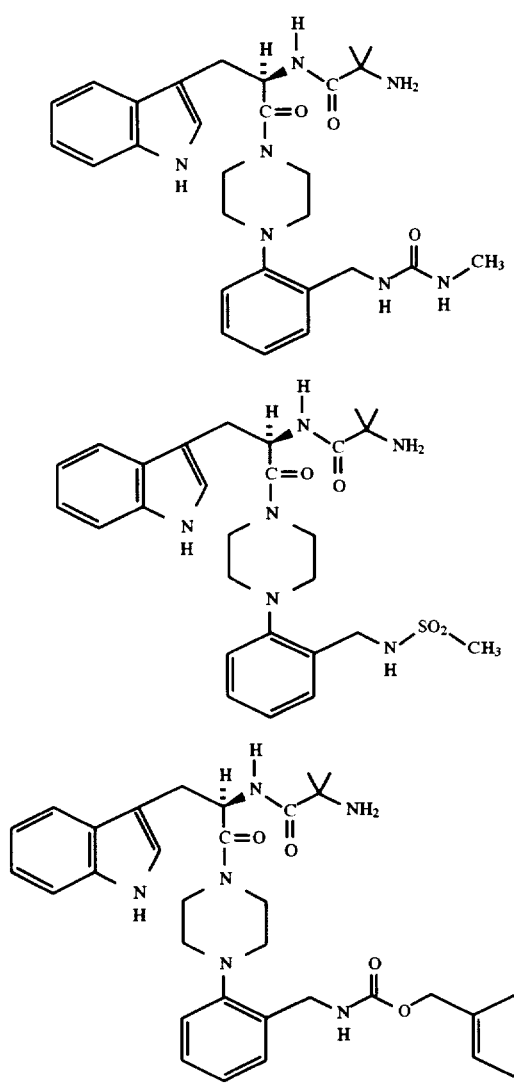
1)
2)
3)
-continued
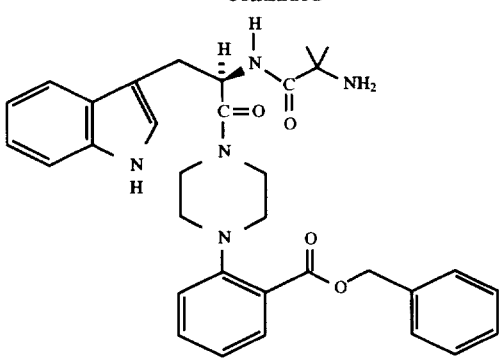
4)
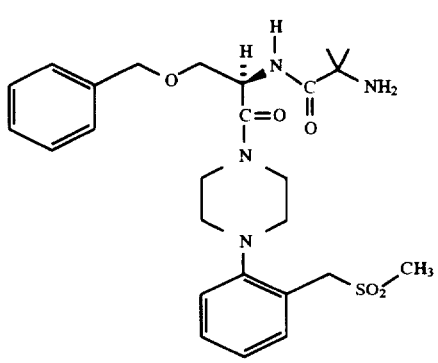
5)
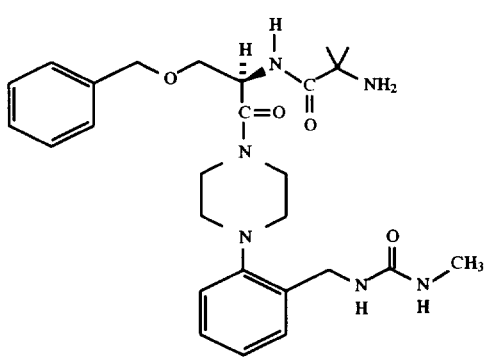
6)
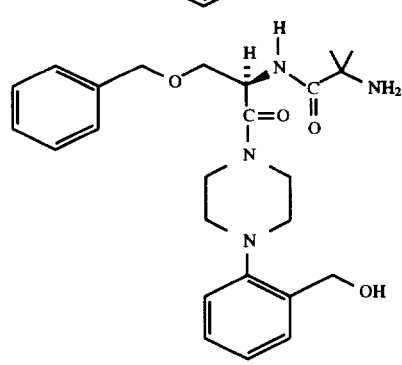
7)

57
-continued
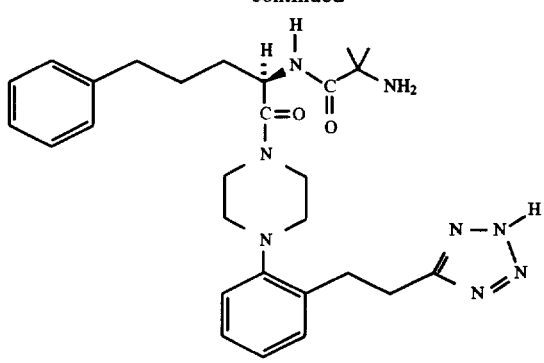
8)
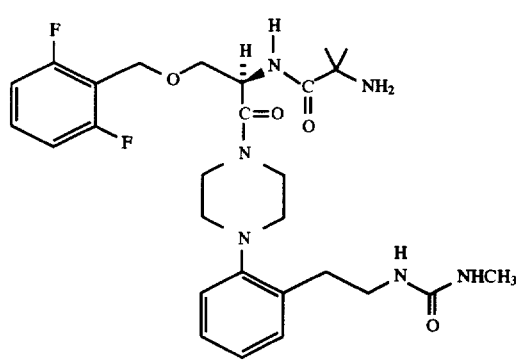
9)
10)
11)
58
-continued
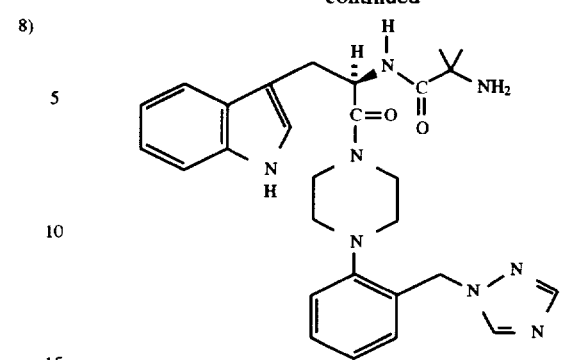
12)
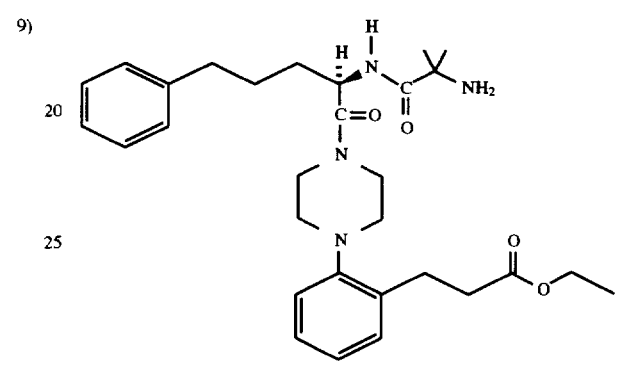
13)
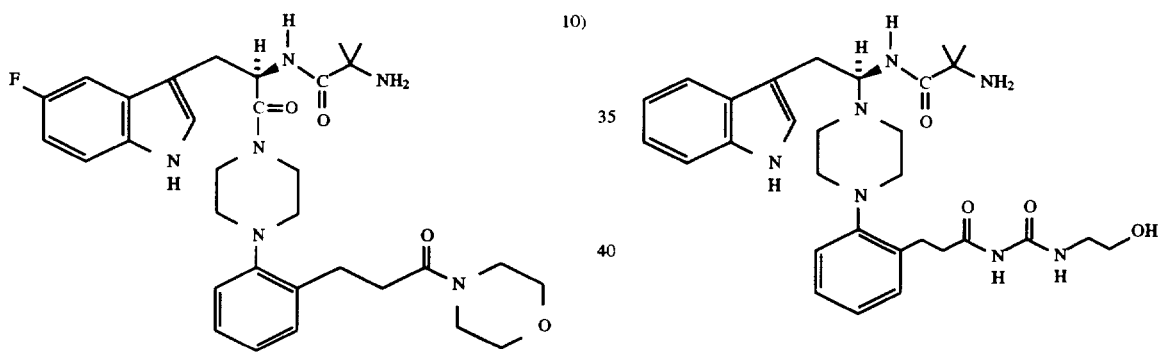
14)
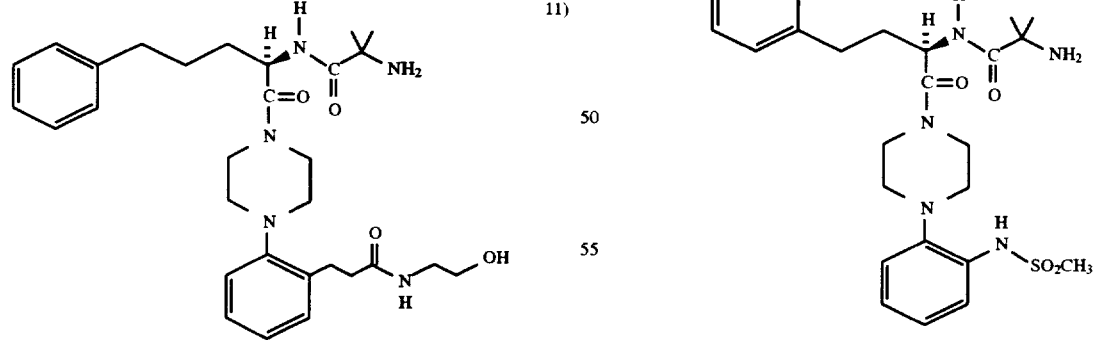
15)

-continued

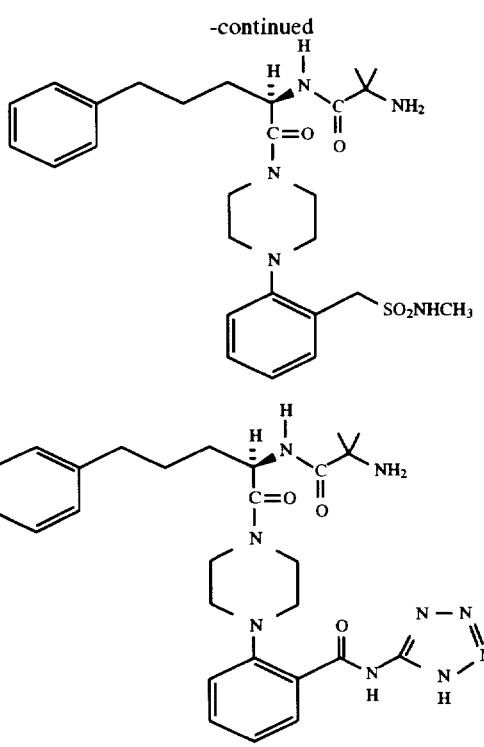

and pharmaceutically acceptable salt thereof.

6. A process for the preparation of a compound of claim 1 which comprises reacting a compound of the formula:

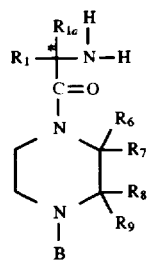

with a compound of the formula

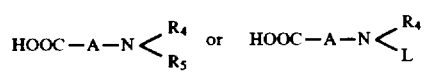

to give compound of formula

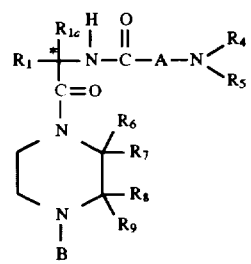

wherein $R_1$, $R_{1a}$, $R_4$, $R_5$, $R_6$, $R_7$, $R_8$, $R_9$, A and B are are as defined in claim 1 and L is a protecting group which is subsequently removed if present and salts are formed if desired.

7. A process for the preparation of a compound of claim 1 which comprises reacting a compound of the formula:

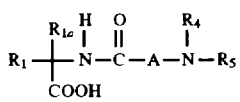

or

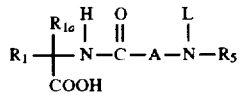

with a compound of the formula

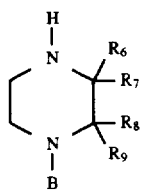

to give compound of formula

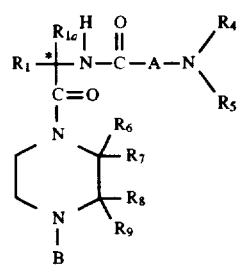

wherein $R_1$, $R_{1a}$, $R_4$, $R_5$, $R_6$, $R_7$, $R_8$, $R_9$, A and B are are as defined in claim 1 and L is a protecting group which is subsequently removed if present and salts are formed if desired.

* * * * *